United States Patent
Keith

(10) Patent No.: US 10,786,592 B2
(45) Date of Patent: Sep. 29, 2020

(54) REACTION CORE SYSTEM FOR PHOTOCATALYTIC PURIFIERS

(71) Applicant: Uvairx, Inc., Castle Rock, CO (US)

(72) Inventor: Jerrod Keith, Castle Rock, CO (US)

(73) Assignee: UVAIRX, INC., Castle Rock, CO (US)

(*) Notice: Subject to any disclaimer, the term of this patent is extended or adjusted under 35 U.S.C. 154(b) by 0 days.

(21) Appl. No.: 15/740,322

(22) PCT Filed: Jul. 7, 2016

(86) PCT No.: PCT/US2016/041282
§ 371 (c)(1),
(2) Date: Dec. 27, 2017

(87) PCT Pub. No.: WO2017/007898
PCT Pub. Date: Jan. 12, 2017

(65) Prior Publication Data
US 2018/0185539 A1  Jul. 5, 2018

Related U.S. Application Data

(60) Provisional application No. 62/189,600, filed on Jul. 7, 2015.

(51) Int. Cl.
*A61L 9/20* (2006.01)
*B01D 53/88* (2006.01)

(52) U.S. Cl.
CPC ............ *A61L 9/205* (2013.01); *B01D 53/885* (2013.01); *A61L 2209/12* (2013.01); *B01D 2255/802* (2013.01)

(58) Field of Classification Search
CPC ... A61L 9/205; A61L 2209/12; B01D 53/885; B01D 2255/802
See application file for complete search history.

(56) References Cited

U.S. PATENT DOCUMENTS

| | | | |
|---|---|---|---|
| 6,238,631 B1* | 5/2001 | Ogata | B01D 53/007 422/186.3 |
| 2002/0081246 A1* | 6/2002 | Tsukada | B01D 39/06 422/186.3 |

(Continued)

FOREIGN PATENT DOCUMENTS

| | | |
|---|---|---|
| DE | 20021301 U1 | 5/2001 |
| DE | 10118165 A1 | 9/2002 |

(Continued)

OTHER PUBLICATIONS

Roth, Energy Consumption Characteristics of Commercial Building HVAC Systems vol. III: Energy Savings Potential (Year: 2002).*

(Continued)

*Primary Examiner* — Sean E Conley
*Assistant Examiner* — Brendan A Hensel
(74) *Attorney, Agent, or Firm* — Polson Intellectual Property Law, PC; Margaret Polson; Christopher Sylvain

(57) ABSTRACT

A photocatalytic reactor housing having a longitudinal axis allowing a fluid to flow through; a frame holding a light source and blades substantially encompassing the light source around the longitudinal axis; each blade having an interior surface facing the light source and an exterior surface opposite the interior surface; at least a portion of the surface of a plurality of the blades having a coating of material with photocatalytic oxidative properties; and the interior surface of the blade configured to redirect some amount of the light emitted onto another portion of substrate of an adjacent blade. In one embodiment the blades are tilted in the radial direction along at least a portion of the blades. In one embodiment the interior surface is configured to reflect some of the light emitted by the light source on to at least a portion of the exterior surface of an adjacent blade.

17 Claims, 19 Drawing Sheets

(56) References Cited

U.S. PATENT DOCUMENTS

| | | | |
|---|---|---|---|
| 2002/0172627 A1* | 11/2002 | Aoyagi | A61L 2/084 422/186.3 |
| 2005/0186124 A1 | 8/2005 | Fink et al. | |
| 2006/0204409 A1* | 9/2006 | Son | B01D 53/32 422/177 |
| 2008/0131331 A1* | 6/2008 | Josserand | A61L 9/205 422/119 |
| 2009/0260592 A1* | 10/2009 | Niwa | F02B 23/101 123/143 B |
| 2010/0129267 A1 | 5/2010 | Akutsu et al. | |
| 2012/0183443 A1 | 7/2012 | Hurley | |
| 2015/0176597 A1* | 6/2015 | Tadokoro | F04D 29/384 416/243 |
| 2016/0083275 A1* | 3/2016 | Kolstad | C02F 1/78 210/748.15 |

FOREIGN PATENT DOCUMENTS

| | | |
|---|---|---|
| JP | H09-187491 A | 7/1997 |
| JP | 2000-084360 A | 3/2000 |
| WO | 2011123578 A1 | 10/2011 |
| WO | 2012044325 A1 | 4/2012 |

OTHER PUBLICATIONS

Carrier, Application of Fans in Commercial HVAC Equipment Carrier Corporation (Year: 2013).*

Written Opinion of the International Searching Authority dated Oct. 25, 2016 in parent international application PCT/US2016/041282.

International Search Report dated Oct. 25, 2016 in parent international application PCT/US2016/041282.

RGF Environmental, "Commercial Air Purification System" (2009) [4 pages].

RGF Environmental, "Commerical Air Purification System—Mini" (2009) [2 pages].

Office Action dated Sep. 30, 2019 in related Chinese application 201680039959.3.

Office Action dated Apr. 14, 2020 in related Japanese application 2017-568433.

Molekule, Molekule Air product webpage, 8 pages, <https://molekule.com/air-purifier-air> (accessed Apr. 20, 2020).

Molekule, Quick Start Guide, 13 pages (2017).

Sharp, FP-A80UW product webpage, 15 pages, <https://shop.sharpusa.com/sharp-true-hepa-air-purifier-with -plasmacluster-ion-technology-for-extra-large-rooms-fpa80uw/> (accessed Apr. 20, 2020).

Sharp, FP-A80U Air Purifier Operation Manual, 32 pages (2011).

Sharp, FP-A80UW Air Purifier Specification Sheet, 1 page (May 31, 2019).

Air Oasis, AO3000G3 product webpage, 6 pages, <https://www.airoasis.com/shop/g3-series/> (accessed Apr. 20, 2020).

Air Oasis, AO3000G3 Product Sheet, 7 pages (Sep. 21, 2015).

Air Oasis, AO3000G3 Owner's Manual, 8 pages (Feb. 15, 2016).

* cited by examiner

REACTION CORE SYSTEM FOR PHOTOCATALYTIC PURIFIERS

CROSS REFERENCE APPLICATIONS

This application claims the benefit of U.S. provisional application No. 62/189,600 filed Jul. 7, 2015, which is hereby incorporated by reference in its entirety for all purposes.

BACKGROUND

Ambient air in any indoor setting can be a major contributing factor in maintaining a healthy living environment. Mold spores, bacteria, viruses, allergens, volatile chemicals (including volatile organic compounds, referred to as VOCs), and the like are frequently present in ambient air, and at much higher concentrations in indoor environments than outdoor air. In addition, surface-borne contaminants, such as bacteria and viruses, are major concerns in modern indoor environments. These pathogens are responsible for many conditions and diseases in the modern world.

Often, indoor environments are much more contaminated than outdoor environments due to the recent construction trend of much tighter building envelopes and energy-consciousness in fewer air exchanges of indoor air. This phenomenon has been much studied and described as 'sick building syndrome' over the last decades.

Many approaches have been implemented to aid indoor air quality. One approach has been Photocatalytic Oxidation (PCO) technology. By utilizing a metal oxide catalyst, often titanium or silicon dioxide (possibly impregnated with other trace elements), irradiated by light, (generally in the ultraviolet spectrum, but not always), and having a fluid of air, water, or other gas or liquid passed over the irradiated surface, certain phenomena have been observed. While the reactions involved with these phenomena are complex, and the exact details of the reaction process may not be fully understood at the current time, much research and testing has been applied to the beneficial applications of the technology.

The process of creating a photocatalytic surface via irradiation of metal oxides with ultraviolet light has since become commonplace in commercial environmental treatment. Certain additive agents (also called doping agents) in the PCO-reactive coating cause an observable shift to the wavelength reactivity of the metal oxide coating, allowing wavelengths outside of the ultraviolet spectrum to induce photocatalytic effects. Although various forms of metal oxides are capable of producing photocatalysis, Titanium Dioxide ($TiO_2$) remains the most popular and preferred due to its beneficial characteristics. $TiO_2$ is a widely available, highly controllable substance with the most effective band-gap energy observed to achieve a highly stable, sustainable, and controllable PCO reaction.

Due to the major role $TiO_2$ has played in the PCO reaction, much time has been spent studying ways of improving the efficiency of the photocatalyst itself. By adding trace amounts of other elements (called doping) to the $TiO_2$ substrate, different characteristics have been observed. Studies have been conducted in adding silver, rhodium, gold, carbon, cesium, nickel, platinum, copper and many other elements have been reported to having impacts on the PCO process.

While there are PCO purification systems available, the current existing systems suffer many deficiencies. Namely, many systems suffer from lower-efficiency designs in passing fluid across the photocatalytic surface. Also, many designs have less efficient ways of harnessing and controlling the light produced by their light source. Many current designs have sought to improve upon these aspects; however, the current industry landscape leaves room for improvement. One area of concern in the current landscape is the propensity of low-efficiency PCO reactors to only partially break down larger molecules (often VOCs) into other, less desirable compounds (called intermediaries). A more efficient PCO reactor design will greatly reduce the number of intermediary compounds generated by a PCO unit.

The foregoing example of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tool and methods which are meant to be exemplary and illustrative, not limiting in scope. In various embodiments, one or more of the above described problems have been reduced or eliminated, while other embodiments are directed to other improvements.

The problems of the prior art can be overcome with a photocatalytic reactor housing having a longitudinal axis of the housing allowing a fluid to flow there through; a frame holding a light source and a plurality of blades substantially encompassing the light source around the longitudinal axis; each blade having an interior surface facing the light source and an exterior surface opposite the interior surface, a length extending along the longitudinal axis and a width extending around the light source; at least a portion of the surface of a plurality having a coating of material with photocatalytic oxidative properties; and the interior surface of the blade configured to redirect some amount of light emitted by the light source on to another portion of substrate of an adjacent blade. In one embodiment of the photocatalytic reactor housing the blades are tilted in the radial direction along at least a portion of the width of the blades. In one embodiment of the photocatalytic reactor housing the interior surface is configured to redirect or reflect some of the light emitted by the light source on to at least a portion of the exterior surface of an adjacent blade One aspect of the present disclosure is to provide a reaction chamber in which photocatalytic activity can be better controlled and adapted to desired applications. This is accomplished by using a stable support material with a photocatalytic coating layer with high adhesion and durability is able to exhibit a higher efficiency in the PCO reaction process than current chambers available. Improved photocatalytic activity can be attained by providing a suitable reaction chamber for the photocatalytic reaction of the present disclosure which is comprised of any single element or any combination of the elements discussed herein. No limitation to a given embodiment with a specific combination of elements is intended or should be inferred.

Another aspect of the present disclosure is a base structure composed of any number of three-dimensionally aerodynamic (or hydrodynamic) or airfoil (or hydrofoil) shapes. By using a shape design that creates less drag across the surface of the photocatalytic coating, a reduction in turbulence across the area the PCO reaction takes place, reduction in backpressure and an increase in laminar flow, an increase in fluid flow across the PCO active surface, and an overall more efficient and controllable photocatalytic reaction may be achieved.

Another aspect of the present disclosure is when the shapes mentioned above may be twisted, lofted, or distorted into any form of a cylinder, helix, or three-dimensional hyperboloid surface. Changing the shape of the structure into a helical or hyperboloid surface can improve control of the fluid through the structure and across the photocatalytic surface to increase the photocatalytic reaction. Additionally, the disclosed housing can affect pressure and velocity across the photocatalytically active surface, which can have an impact on the output of the photocatalytic reaction process. Helical or cyclonal fluid flows may be formed as the fluid exits the structure. These fluid flows may improve the stability and efficiency of the photocatalytic reaction.

Another aspect of the present disclosure is that the base structure may be comprised of a tapered helical or three-dimensional hyperboloid surface. Changes to the shape of the surface in the transverse direction can be used to control the fluid pressure as it moves through the structure and across portions of the photocatalytic surface to increase the photocatalytic reaction. Certain tapers of the structure may also be used to better use the orientation and output of the light source used to power the photocatalytic reaction.

Another aspect of the present disclosure is to improve the efficiency of the reaction per amount of light emitted by reclaiming and actively or passively refocusing previously used light onto another active surface or other desired area. Nearly all metal oxides that exhibit photocatalytic reactivity do not utilize 100% of light that comes in contact with the surface in powering the photocatalytic reaction (TiO2 has been observed near 70% efficiency at 90° irradiation with ultraviolet light). By redirecting and refocusing any light not utilized in the reaction back onto another photocatalytically reactive surface, an increase in photocatalytic efficiency may occur. Refocusing a wider area of unutilized light onto a smaller area of photocatalytic reactive surface will allow for an area of higher intensity of redirected light; this may allow for higher areas of photocatalytic reactivity.

Another aspect of the present disclosure is coating the various surfaces of the base structure in one or more formulations of the photocatalytic material. Coating different areas of this structure with different formulations of photocatalytically reactive metal oxides or doped variations thereof will allow for different complex reactions to form on or above the surface of the photocatalytic substance. This diversity of photocatalytic surfaces and reactions can be tailored to react with specifically targeted elements of concern.

Another aspect of the present disclosure is that the base structure may be stationary with an exterior fluid movement system or able to revolve to act as an independent dynamic fluid system. These elements may be designed in a way that allows the reaction chamber to be powered to act as a fan or pump to be a self-contained reactor system.

Another aspect of the present disclosure is that the base structure can be scalable to nearly any size or emission length of light output. The previously mentioned elements of design may be presented at different sizes and configurations to best accommodate the source of light or desired characteristics of photocatalytically active surfaces.

In addition to the exemplary aspects and embodiments described above, further aspects and embodiments will become apparent by reference to the accompanying drawings forming a part of this specification wherein like reference characters designate corresponding parts in the several views.

Figure 1:
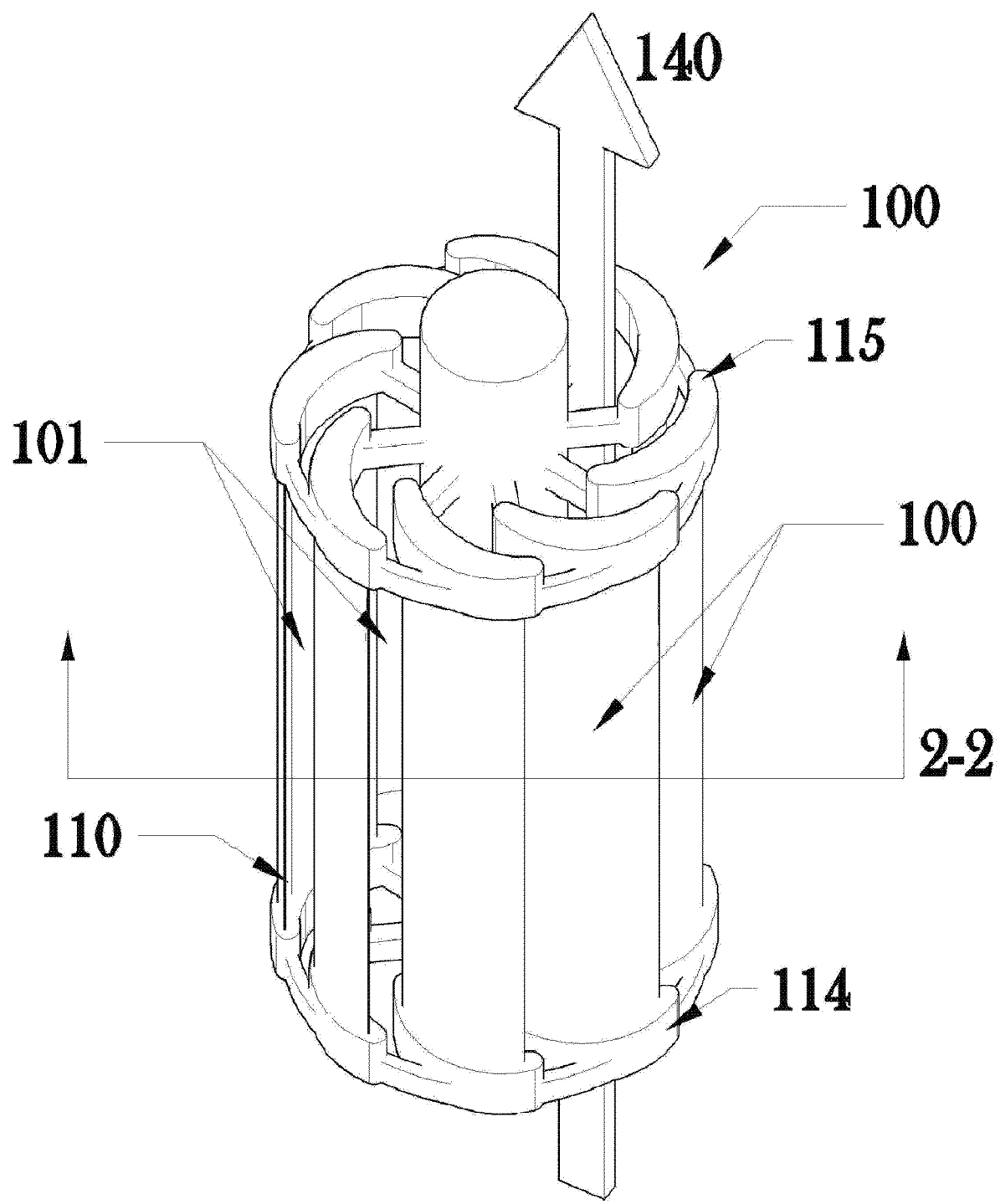
FIG. 1 is a perspective view of a one embodiment of a housing forming a reaction chamber.

Before explaining the disclosed embodiment of the present invention in detail, it is to be understood that the invention is not limited in its application to the details of the particular arrangement shown, since the invention is capable of other embodiments. Exemplary embodiments are illustrated in referenced figures of the drawings. It is intended that the embodiments and figures disclosed herein are to be considered illustrative rather than limiting. Also, the terminology used herein is for the purpose of description and not of limitation.

DETAILED DESCRIPTION

The present disclosure is directed to a system for and a method of making an improved PCO purification system using the specified shapes of a housing that is coated with any type of metal oxide. In the depicted embodiment, a titanium dioxide based mixture is coated thereon. The present housing allows for greater control of fluid flow and light containment, easier manufacturability, and allows for the parts to be coated individually, allowing for greater control of the coating process. Each one of these elements independently creates a PCO reaction chamber that is more efficient and offers higher desirable characteristics of the PCO reaction of the prior arts. The elements can be combined in any number of ways to create the conditions desired for any given installation. It is expected that careful consideration of the starting conditions, fluid flow and desired results will allow a user to choose among the possible different element to create a PCO reaction chamber that is specifically tailored to a broad range of air (or water or other fluid) quality conditions and installation locations.

The disclosed structure presents advantages over conventional structures by limiting turbulence, offering a more controlled fluid flow, containing more of the light emitted within the reaction chamber, redirecting and refocusing light not readily absorbed on first contact with the PCO-reactive coated surface onto another surface coated in PCO-reactive coating, controlling the pressure and velocity of the fluid flowing across the PCO-reactive surface, and offering the ability to easily integrate several different formulations of PCO-reactive coatings to tailor the reaction to the desired target application, or allow for the reaction chamber to be used as its' own fan or pump to move fluid across the PCO-reactive surface.

In one disclosed embodiment of the disclosure, Degussa P25 titanium dioxide particles are used. Degussa P25 titanium dioxide particles are composed of approximately 70-80% titanium dioxide in anatase form and of approximately 20-30% titanium dioxide in rutile form. The average particle size of Degussa P25 titanium dioxide agglomerate particles used in a preferred embodiment of this invention is approximately 20 nm. Titanium dioxide particles having other average particle sizes or formulations are considered to be within the scope of the invention.

The Degussa P25 titanium dioxide is then mixed with other trace elements (silver, copper, rhodium, carbon, etc.) which are chosen to achieve the desired reaction components, and applied to the surface of the structure via sol-gel, sputtering, spraying, dipping, or other application methods. Other methods of coating, adhesion, or affixing (either mechanically bonded or chemically bonded) of any photocatalytically active metal oxide, alloy, or combined material is considered to be within the scope of the invention Below is a table containing a number of known and studied doping agents, photocatically active substances. As research continues, many other effects on the PCO reaction may be found, and this list is not meant to be inclusive of every viable compound, but to expound on some of the known chemical agents that have had an observed impact on the photocatalytic reaction process.

Table 1 shows a sample listing of some known base materials to use for doping agents.

| Base Materials | Subset | Performance Characteristics |
|---|---|---|
| Titanium Dioxide | Rutile | Higher band-gap energy required than anatase due to differences in crystalline structure. |
| | Anatase | Generally higher PCO characteristics to rutile due to different molecular structure than rutile. |
| | DeGussa P25 | 70% anatase, 30% rutile (typically) |
| Silicon Dioxide | Silica Gel | Davisil 626; increased porosity; |
| ZnO | Substrate | Enhancement of quantum efficiency |
| $Au/TiO_2/SiO_2$ | Sandwich | Antimicrobial surfaces, photonic devices |
| Graphene/Carbon Composite | 88.68% Carbon, 0.79% H, 1.11% N | Carbon nanofibers containing micropores for increased photocatalytic activity in visible light |
| Glass | Florine doped Tin Oxide | Increase in photoelectrochemical (PEC) performance, increasing reaction efficiency used in spray coating of $TiO_2$ films. |
| Various | Spraying power used; deposition efficiency of 65.1% @ 43.8 KW | Higher spraying power and shorter distances result in higher deposition efficiency. Thickness 350-420 nm using grain size of $TiO_2$ of 20-50 nm |
| TiN—Ag | Polyester surface; 50 nm thickness, TiN, 50 nm Ag; Ag = 0.023 wt % TiN = 0.29 wt % | Visible light activation enhancement for inactivation of viruses and bacteria. |

Table 2 lists a sample of known doping formulations that could be used with the present disclosure.

| Doping Agent | General Concentration | Performance Characteristics |
|---|---|---|
| Copper (Cu) | 0.2-5 wt % | High surface area increasing photocatalytic activity, as well as other effects |
| Rhodium (Rh) | 0.5-2.5 wt % | Deposited in a ph = 11; NOx reduction enhancement, as well as other effects |
| Silver (Ag) | 0.25-5 wt % | Reduction in recombination rate of electron hole pairs while increasing the surface area of particles resulting in enhanced photocatalytic activity, as well as other effects |
| Silica | 25 mol % | Higher surface area and acidity, improved adsorption, as well as other effects |

-continued

| Doping Agent | General Concentration | Performance Characteristics |
|---|---|---|
| Carbon (C) | 20:1 mass ratio; 2 wt % | Varying amounts to achieve specific performance targets, elevated destruction of acetaldehyde; visible light and dark enhancement; use of SWCNTs, as well as other effects |
| Nickel (N) | 3-5 wt % | Visible light activation, as well as other effects |
| Iron (Fe) | 3-4 wt % | Removing Azo dyes from wastewater, enhanced removal of formaldehyde, as well as other effects |
| $TiO_2/SiO_2/Mn$ | Mn = 10 mol % | Enhanced decomposition of acetaldehyde, as well as other effects |
| TiN, TiN—Ag | Sputtered $1.4 \times 10^{15}/cm^2$ s | Enhanced visible light activation for deactivation of bacteria and viruses, as well as other effects |
| Nitrogen | 15-22% | Enhancement of visible light activation, as well as other effects |
| Vanadium | 2 wt % | Elevated destruction of acetaldehyde, visible light and dark enhancement, as well as other effects |
| Manganese (Mn) | 2-3 wt % | Elevated destruction of acetaldehyde, visible light and dark enhancement, as well as other effects |
| Silicon Dioxide ($SiO_2$) | 5-10 mol %, 25% mol % | Enhanced adsorption capacity for VOCs, mercury, promotes superhydrophilicity for self-cleaning surfaces, as well as other effects |
| Zinc (Zn) | 3-5 wt % | Enhanced photocatalytic activity, as well as other effects |
| Iron Oxide ($Fe_2O_3$) | 5 wt % | Higher photocatalytic efficiency deactivating formaldehyde, as well as other effects |
| Tungsten Trioxide ($WO_3$) | 1-3 wt % | Promotes superhydrophilicity, increased photocatalytic activity in visible light, as well as other effects |
| Silver Nitrate ($AgNO_3$) | 4-5 wt % | Enhanced photocatalytic activity, as well as other effects |
| Manganese Oxide (MnO) | 1 wt % | Higher absorbance in UV region, protection against corrosion, as well as other effects |
| Vanadium Oxide ($V_2O_5$) | 1 wt % | Higher absorbance in the UV region, protection against corrosion, as well as other effects |
| Zirconium (Zr) | Ti:Zr = 1:2 | Increased surface area, enhanced photocatalytic activity, as well as other effects |
| Zirconium Dioxide ($ZrO_2$) | 10 wt % | Inorganics support and adsorbent, as well as other effects |
| Graphene Oxide (GO) | 1-5 wt % | Accelerated sedimentation rates in wide PH range, as well as other effects |
| Sulphur (S) | 0.3-5 wt % | Enhancement of VOC destruction, as well as other effects |
| Zirconium Silicate ($ZrSiO_4$) | ~15 mol % | Control of refractive index, as well as other effects |
| Cadmium Sulfide (CdS) | 5 wt % | $Ch_4$, $CO_2$ reduction, as well as other effects |
| Aluminum (Al) | Ti:Al = 1:2 | Enhanced photocatalytic activity, as well as other effects |
| Niobium (Nb) | Ti:Nb = 1:2 | Enhanced photocatalytic activity, as well as other effects |
| Cerium (Ce) | 5 mol % | Visible light enhancement, greater recombination enhancement, VOC destruction enhancement, as well as other effects |
| Zinc Oxide (ZnO) | 2-5 wt % | Enhances quantum efficiency, as well as other effects |
| Gold (Au) | 1-3 wt % | Elevated photocatalytic activity, as well as other effects |
| Palladium (Pd) | 0.08 wt % | Enhancement in visible range targeting VOCs, as well as other effects |
| Gold-Palladium (Au—Pd) | 1.9/0.08 wt % | Enhancement of decontamination of citral, as well as other effects |
| Platinum (Pt) | 0.75-3 wt % | Improvement of photocatalytic efficiency, enhancement of performance in visible range, reduces CO and formaldehyde, as well as other effects |

-continued

| Doping Agent | General Concentration | Performance Characteristics |
| --- | --- | --- |
| Platinum-Iron Oxide ($PtFeO_3$) | Pt = 1-2 wt %, FeO3 = 4-6 wt % | Elevated efficiency on volatile organic compounds, especially formaldehyde, as well as other effects |

A light source is enclosed by the disclosed housing which can emit light capable of exciting the PCO-active surface (for most formulations of $TiO_2$, with wavelength below 400 nm) that excites the surface of the metal oxide coating causing it to exhibit PCO-reactive phenomena. Most often ambient air will be the fluid passed through the housing and effected by the PCO-reactive phenomena. Other fluids can be used as well. The remainder of the discussion of the disclosed housing will be discussed in terms of air, but it is to be understood that any chosen fluid could be used. No limitation is intended, or should be inferred.

Figure 2:
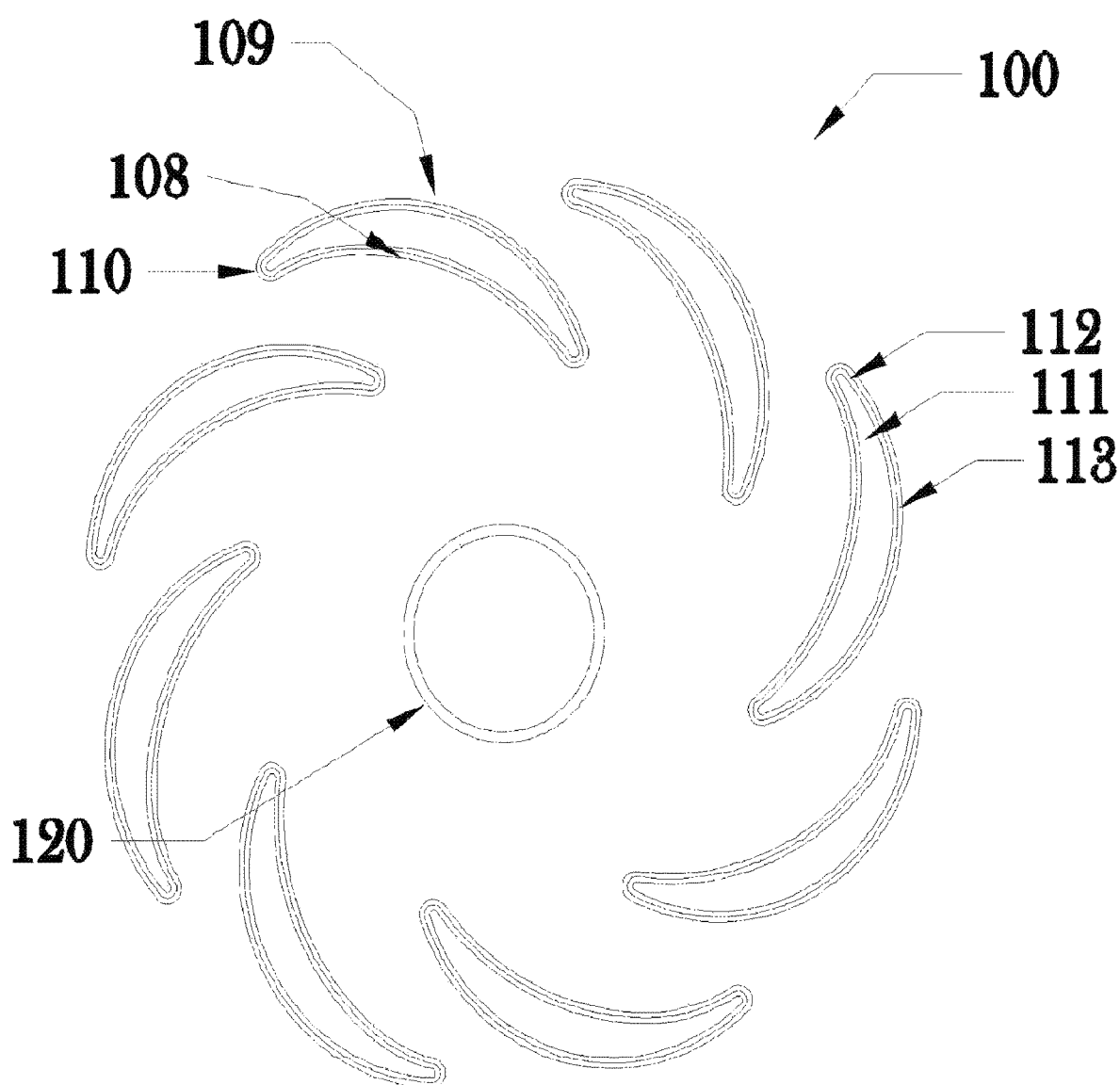
FIG. 2 is a section cut of one of the embodied shapes with a detailed view of areas of coating.

Referring first to FIGS. 1 and 2, air or other fluid is flowed through the housing 100 containing a light source 120 along the longitudinal axis, indicated by arrow 140, across the reactive surfaces 101 allowing the PCO reaction to take place. The housing 100 has a chosen number of blades 110 that extend along the longitudinal axis of the housing. As seen in FIG. 2, the transverse profile of the blade 110 is an aerodynamic shape with the inner wall 108 that can be straight line segments or concave arc, spline, or parabolic surfaces, and the outer wall 109 can be made up of straight line segments or convex arc, spline, or parabolic surfaces. In the depicted embodiment, the cross sectional shape of blades 110 is generally arch shaped. In most embodiments, the blades 110 will have an aerodynamic shape to encourage fluid flow through the housing with lessoned turbulence relative to prior art designs. This also allows the fluid flow to be directed on the surfaces containing the PCO-reactive coatings.

These blades 110 have a base structure 111 which is coated in an optional substrate material 112 in the depicted embodiment, and then coated in a formulation of metal oxide 113. Depending on the application and the material chosen for the base structure 111, the substrate layer may not be required in some embodiments. The blades 110 are held in place by a first retainer 115 and a second retainer 114 mounted on the ends of blades 100 as seen in FIG. 1. The light source 120 is mounted in the central axis of the housing as seen in FIG. 2. The light source 120 depicted is a T-5 UV light bulb. A wide range of acceptable light sources are known in the art, no limitation to the depicted embodiment is intended or should be inferred.

Figure 3:
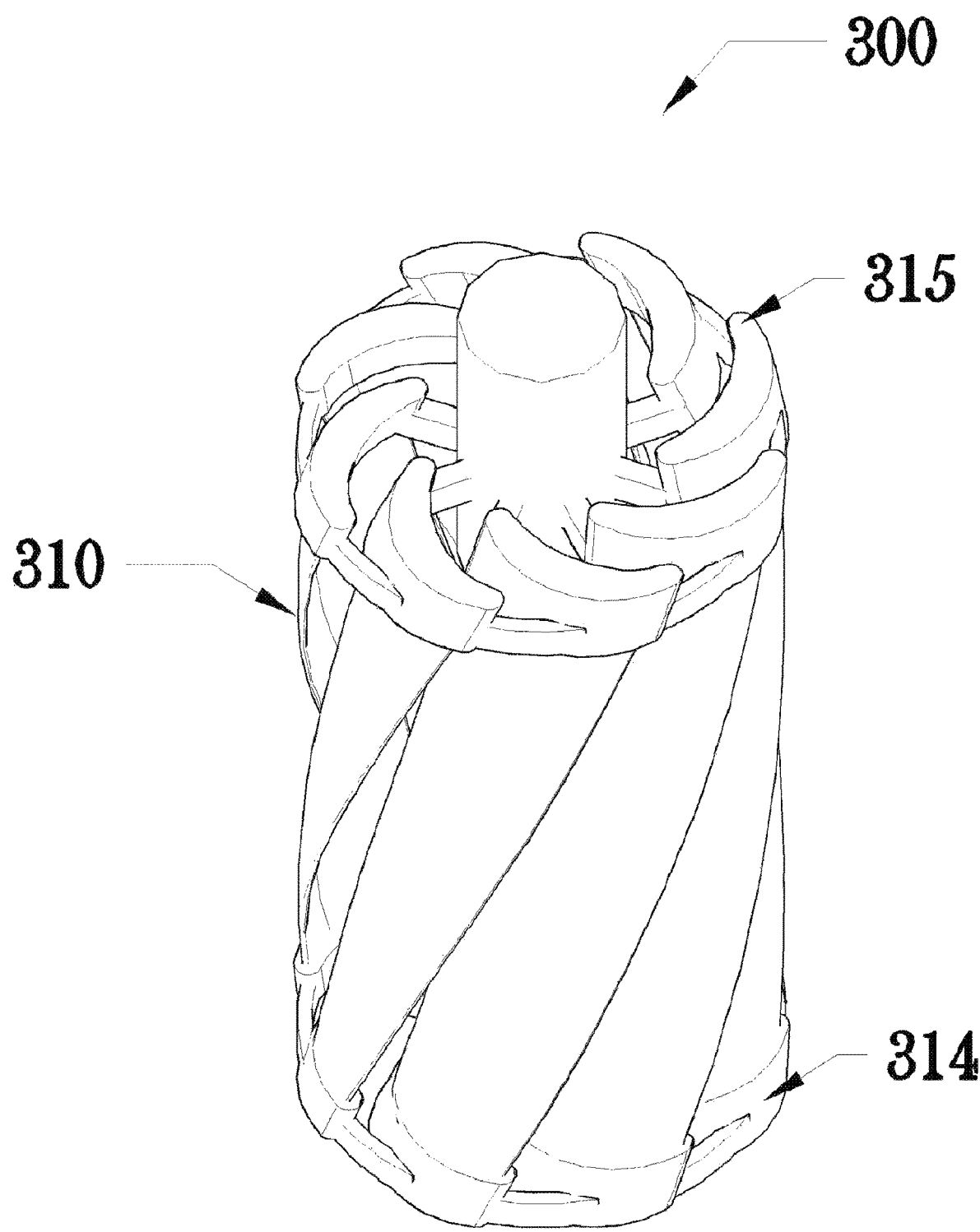
FIG. 3 is a perspective view of a second embodiment of a housing forming a reaction chamber.

Referring next to FIG. 3, a second embodiment of the housing 300 is depicted Housing 300 has blades 310 which are twisted along the longitudinal axis. The blade 310 can be lofted, extruded, or distorted into any form of a cylinder, helix, or three-dimensional hyperboloid surface to better conform to characteristics of light emission or airflow dynamics in addition to the shape shown in FIG. 3. These blades are held in upper retainer 315 and a lower retainer 114.

Figure 4:
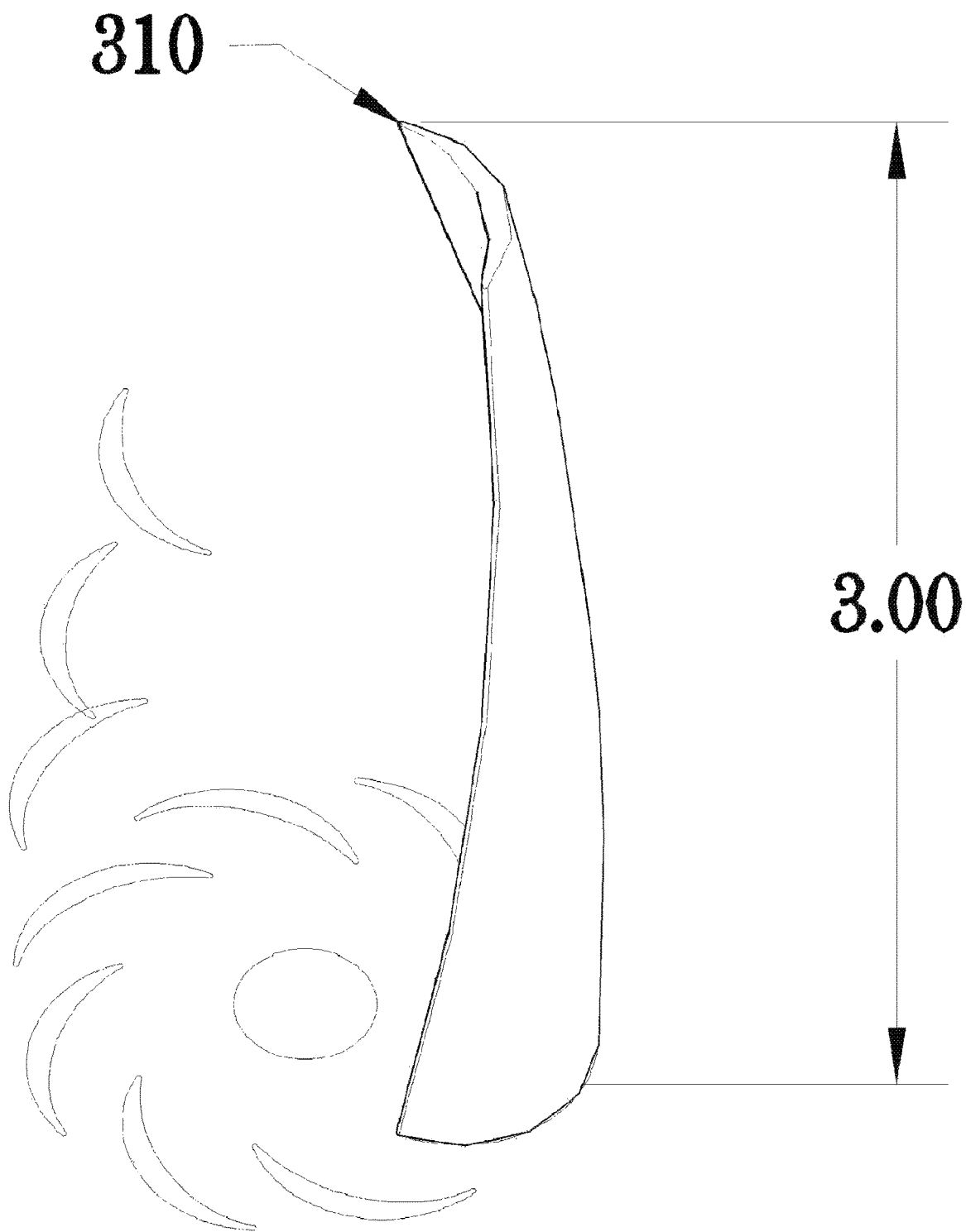
FIG. 4 is a detail of a singular blade similar to that shown in FIG. 3.

FIG. 4 is a perspective view of blade 310 with a helical twist shown in FIG. 3. This design is comprised of the blade design outlined in FIG. 1 and FIG. 2 lofted or extruded with a 27° twist per inch. The height of this blade design is 3" overall in the depicted embodiment. This design, however, may be scaled to a different size, and have a tighter or looser twist (in either clockwise or counter-clockwise direction) dependent upon the desired characteristics of the PCO reaction contained in the reaction chamber.

Figure 5:
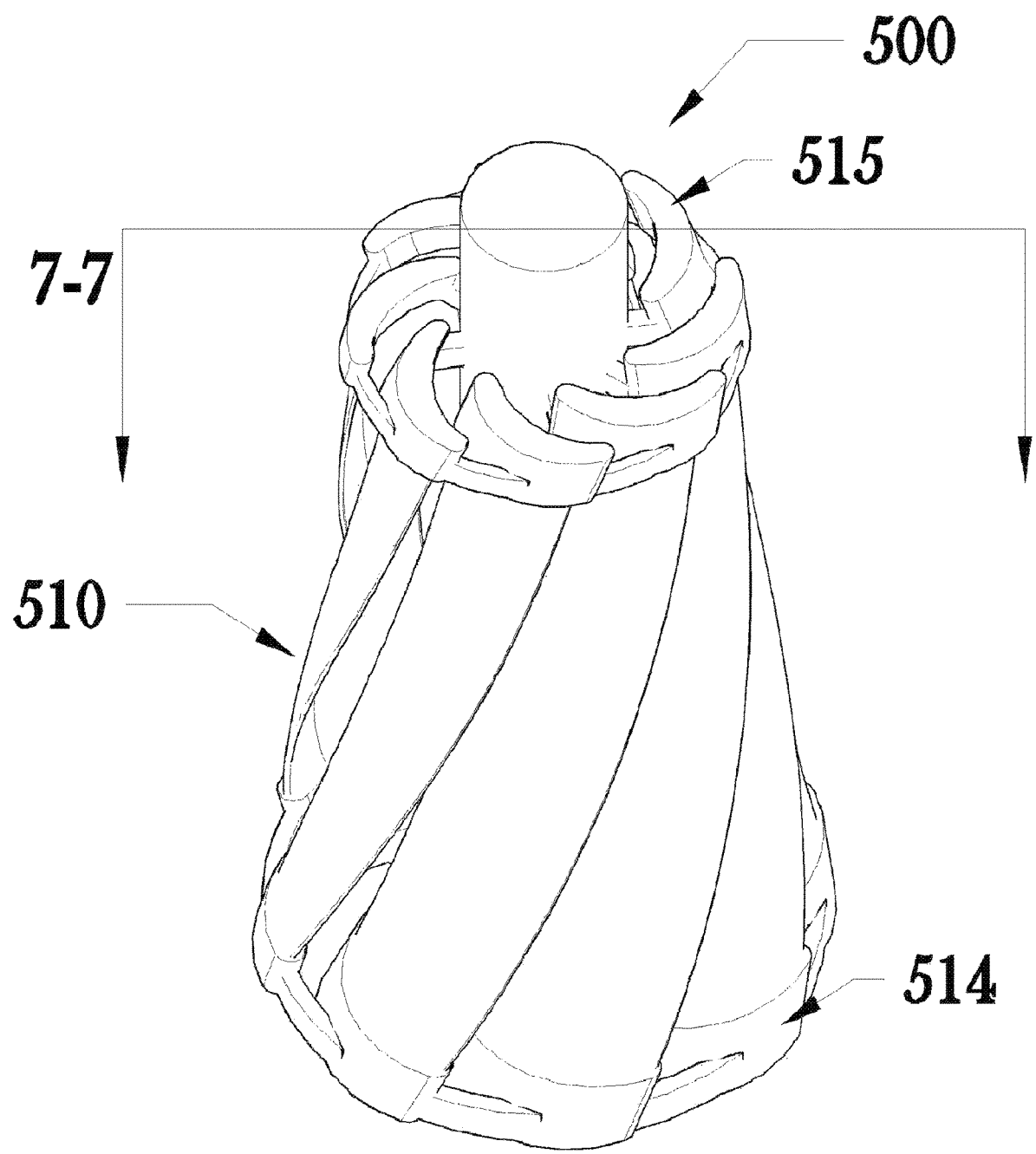
FIG. 5 is a perspective view of a third embodiment of a housing forming a reaction chamber.
Figure 6:
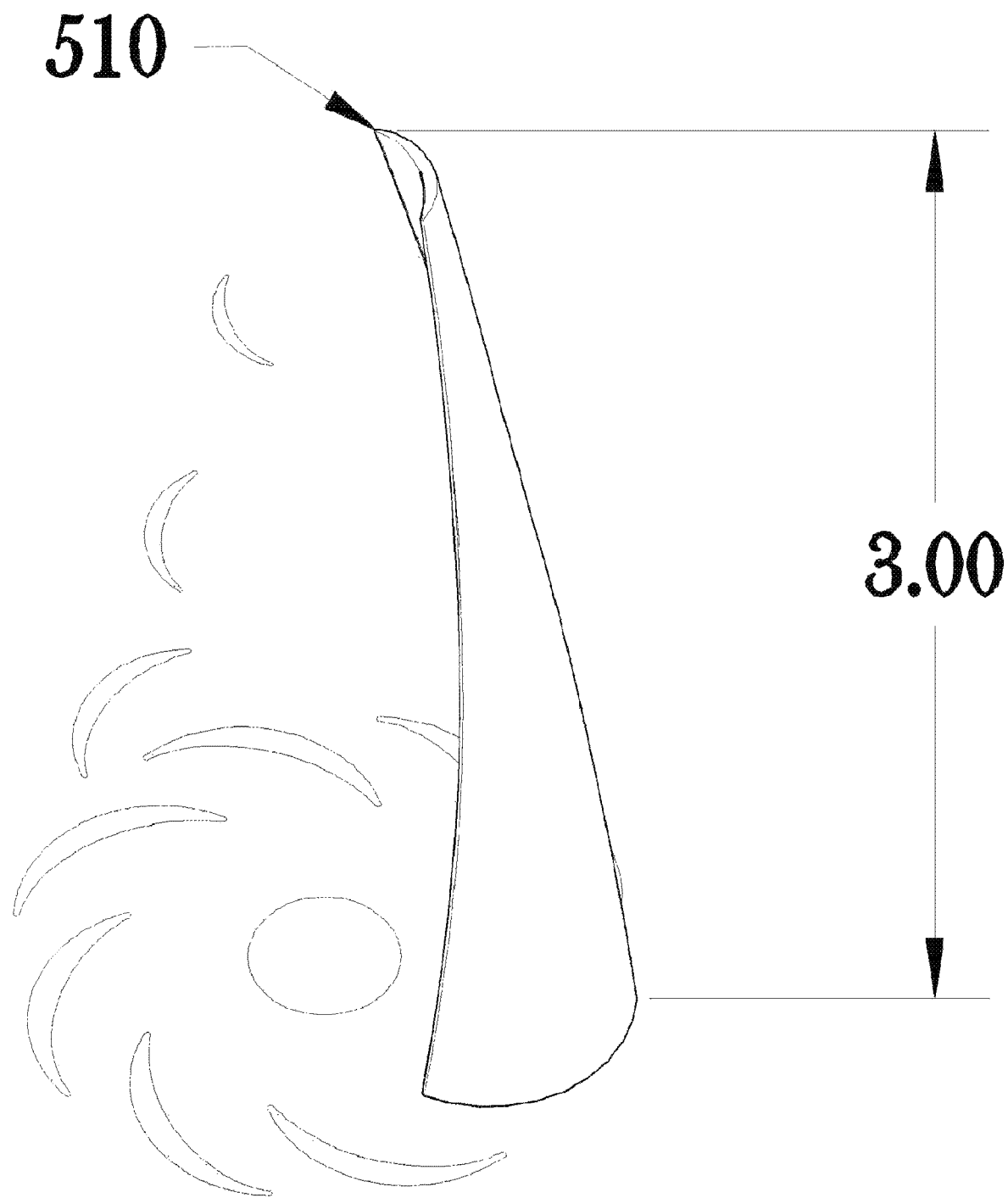
FIG. 6 is a detail of a singular blade similar to that shown in FIG. 4.

In a fourth embodiment, the blades of the disclosed housing can also be tapered, distorted, or shaped in three dimensional or longitudinal axes to better conform to characteristics of light emission or fluid flow dynamics, as shown in FIG. 5. FIG. 6 is a representation of the blade 510 with a helical twist as well as a transverse taper shown in FIG. 4. This design has a blade design as outlined below that is lofted or extruded with a 27° twist per inch, as well as being tapered down 20% per inch. The height of this blade design is 3" overall in the depicted embodiment. This design, however, may be scaled to a different size, and have a tighter or looser twist (in either clockwise or counter-clockwise direction) dependent upon the desired characteristics of the PCO reaction contained in the reaction chamber.

Figure 7:
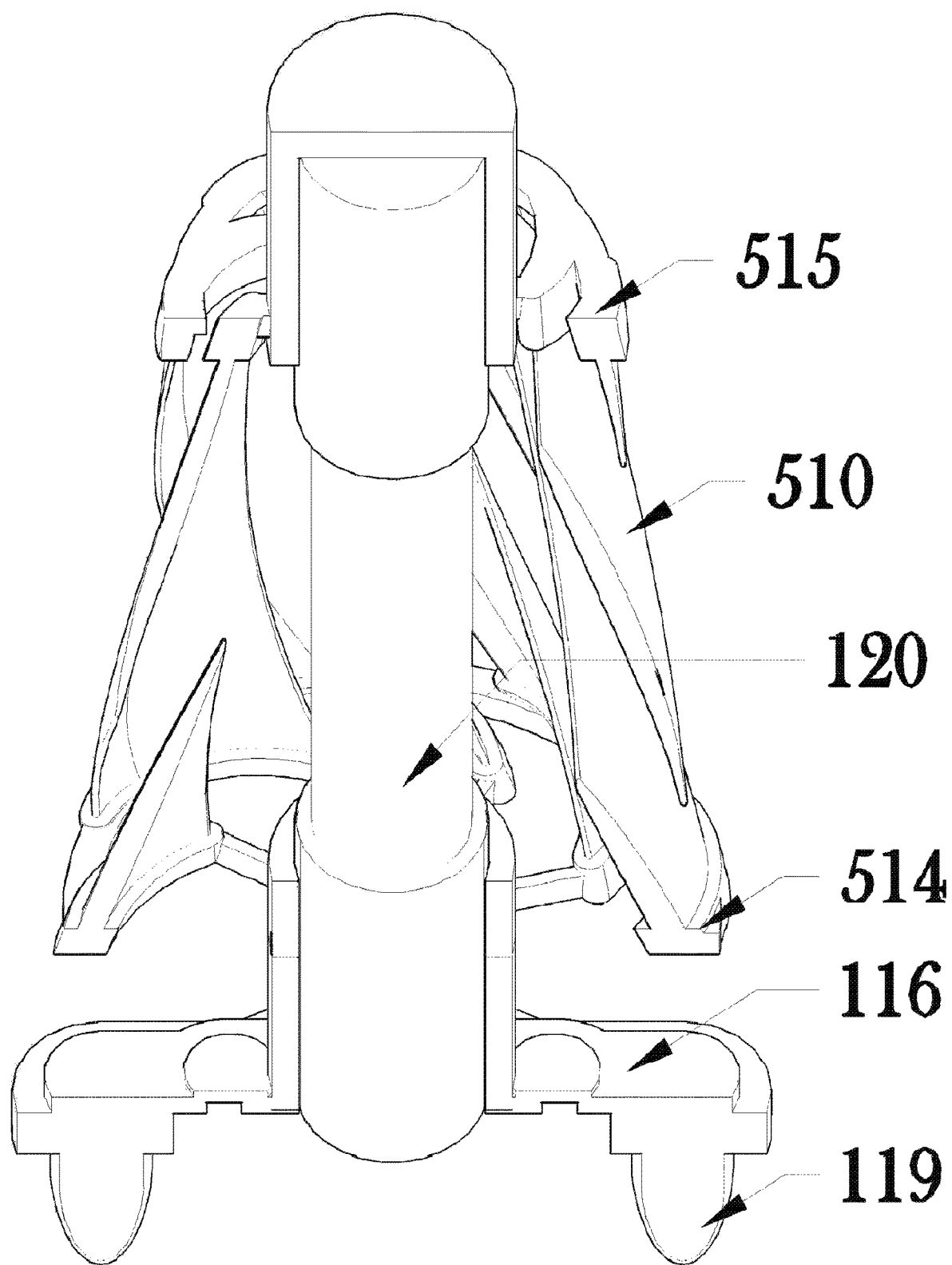
FIG. 7 a sectional view taken along line 7-7 of FIG. 5 with a support bracket added.
Figure 8:
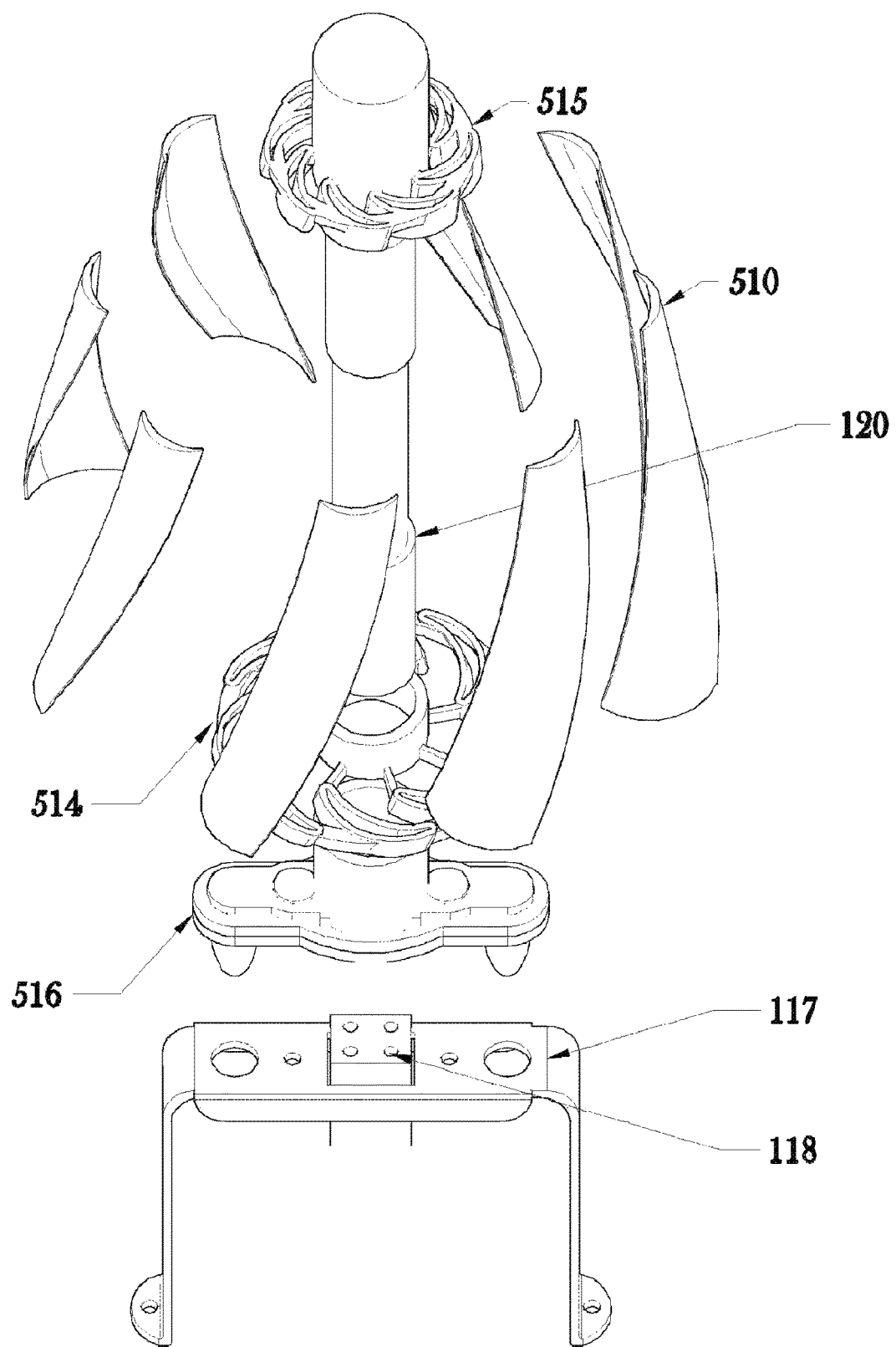
FIG. 8 is an exploded view of the embodiment of FIG. 5.

FIG. 7 shows a section cut of an aspect of the fourth embodiment of the structure of the reaction chamber design suitable for consumer use, including lower blade and lamp support 514, upper blade and lamp support 515, and lamp alignment support 516. Detail on the alignment support is highlighted in FIGS. 10a and 10b. This embodiment shows blades 510 that are distorted in both transverse and longitudinal directions to better control both the light emitted from the T-5 UV lamp 120 and fluid flowing through the reaction chamber along the longitudinal axis (flowing from the lower portion, through the reaction chamber, and escaping the chamber across the PCO surface between the blades.) Detail in FIG. 8 is an exploded view of the blade 510 and lower retainer 514 highlighting how the blades slot into the retainer. The fit in these retainers can be tapered at the same angle as the blade, or the blades may be 'straight' (without twist or taper) on the ends to slot into a transverse-cut retainer.

FIG. 8 is an exploded view of the preferred embodiment shown in FIG. 5. The upper retainer 515 is used to support the upper portion of the T-5 UV lamp 100 as well as the upper edge of the blades 510. The upper retainer may have holes or passages to allow for the fluid to pass through, or may be enclosed to fully redirect the fluid through the surfaces between the blades. The lower retailer 514 is used to support the lower end of the blades, and hold them in constant position in relation to the light source. Both retainers may either be hard affixed (glued, ultrasonically welded, or some other method of adhesion) to the lamp 100 or alignment pins 116 or they may spin free. This is discussed in detail on FIG. 18. Both retainers may or may not be coated in the same, or different, PCO coating as the blades.

The T-5 (or other design) of plug 118 and plug housing 117 seen in FIGS. 7, 8 and 10 a and b are simply one method into which this preferred embodiment may attach, and are just shown for reference. This does also show the relationship in how the alignment pins 119 are able to guide, direct, and may help support the pins 140 of the lamp 100 into the receptacles 141 in the plug 118.

Figure 9:
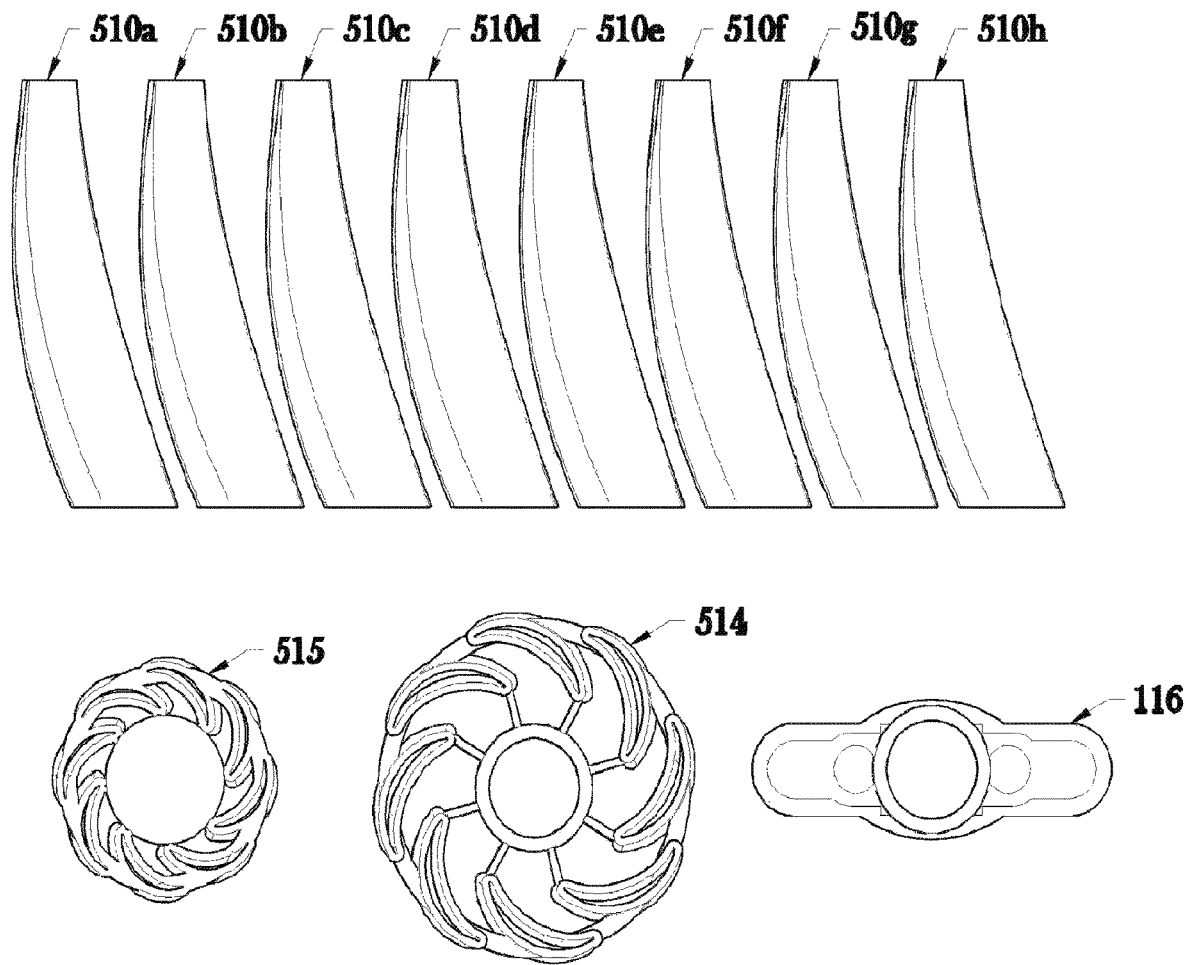
FIG. 9 is a disassembled view of components in FIG. 5.

One aspect of the disclosed housing is the ability to coat individual blades with different formulations of PCO-reactive coating to specifically tailor a finalized reaction chamber to be able to target specific PCO characteristics based on the needs of the end application. FIG. 9 shows the complete assembly of the embodiment in FIG. 5 and FIG. 6 disassembled. Each of the blades 510 could be coated with a specific formulation of PCO coating shown here as 510*a*, 5100*b*, 510*c*, etc.), inserted into the upper blade and lamp support 515 with the lamp, held in place by the lower blade and bulb support 514, and held in place by the lamp alignment support 116. Though advanced coating techniques, multiple coating formulations may be used on a single substrate. For example, one side of a blade could be coated with one formulation and the other side with a second formulation. The various combinations of formulations could be used to either solve known deficiencies of current formulations or to design a housing for a specific need at a specific location. The second formulation could be chosen specifically to break down the known intermediaries of partial reactions of the first formulation, for example. This could be done with as many different formulations as desired.

Figures 10A, 10B:
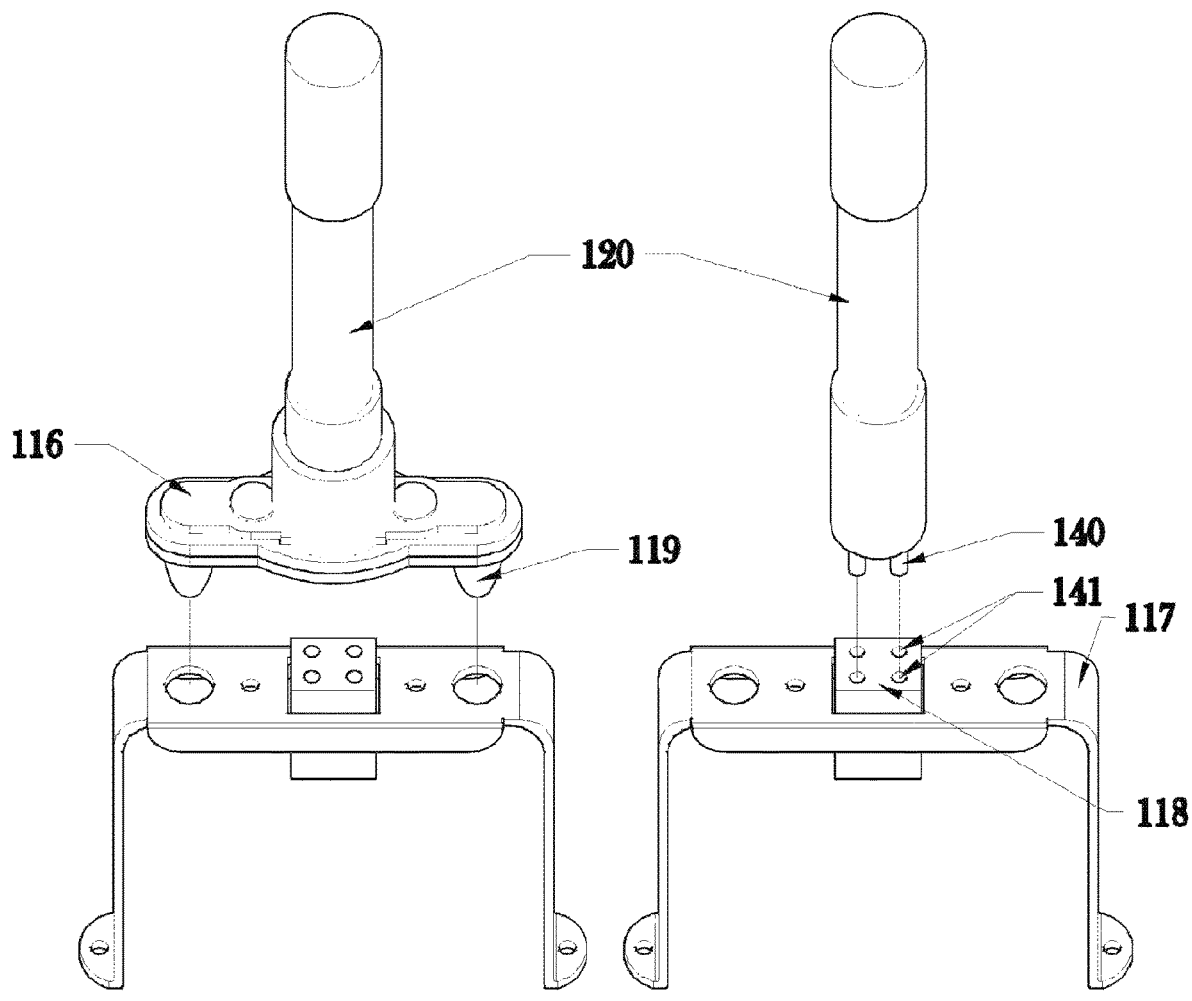
FIGS. 10a and 10b are partial exploded views of the lamp with the receptacle.

FIGS. 10*a-b* shows the design of the alignment pins 116 which are designed to align the pins of the lamp 120 to the receptacles of the power plug 118. The alignment guides 119 are larger than the pins of the lamp, are generally parabolic in section (but not required to have that specific shape), and are used to guide the pins 140 of the lamp into the power plug 141. This makes installation of the reaction chamber into its' specific application by the end user much easier. With the alignment guides 119 being larger than the pins of the lamp, they give more tolerance to being able to install the reaction chamber correctly, and have the lamp seat firmly and accurately into the receptacle.

Figure 11:
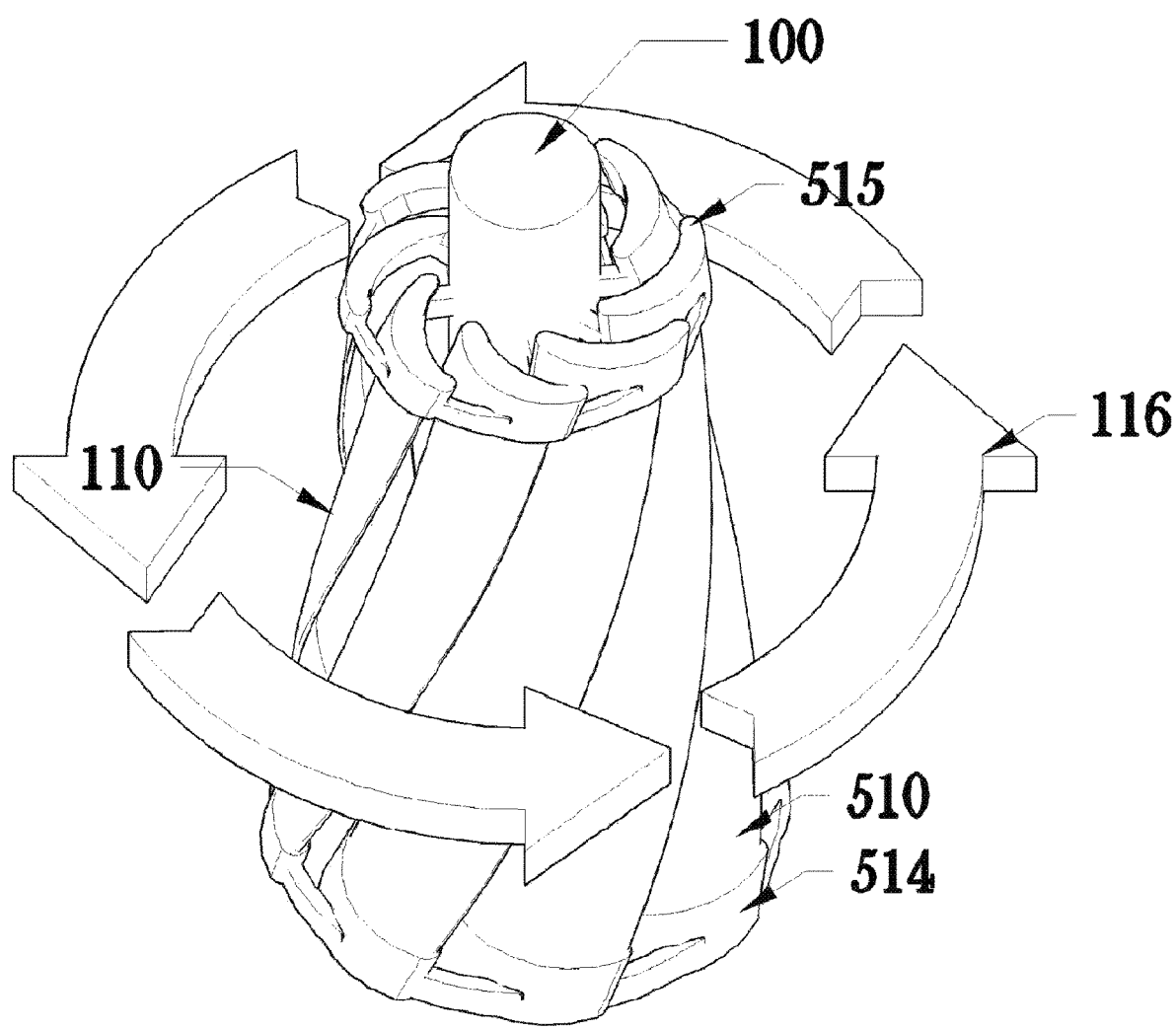
FIG. 11 is a perspective view of the reaction chamber with arrows to show the possible rotation.

This design also has the possibility to work as its' own power source for fluid flow. FIG. 11 shows that by spinning the upper and lower blade retainers 514 and 515 and the blades 510, the shape of the blades will pull the fluid across the PCO-reactive surface. The lamp 100, plug 118 and plug housing 117 may be stationary or may move with the reaction chamber. This allows the disclosed housing to be used in systems where fan, pump, or other fluid movement methods are not desirable, and/or efficient. This spinning of the housing causes the fluid to move through the reaction chamber without an external fluid movement system. Rotation of the housing is shown by arrow 116.

Figure 12:
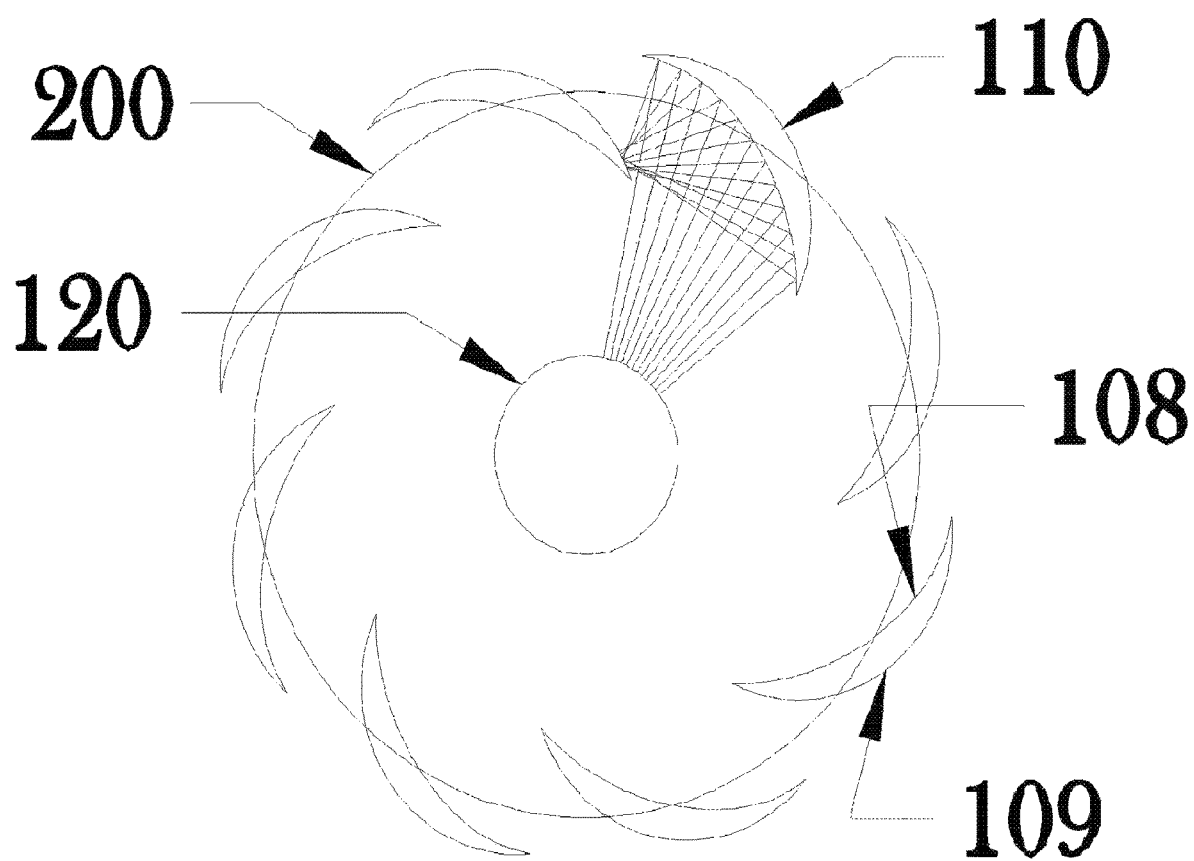
FIG. 12 is a cross sectional one of the embodied shapes showing of the light redirection.
Figure 13:
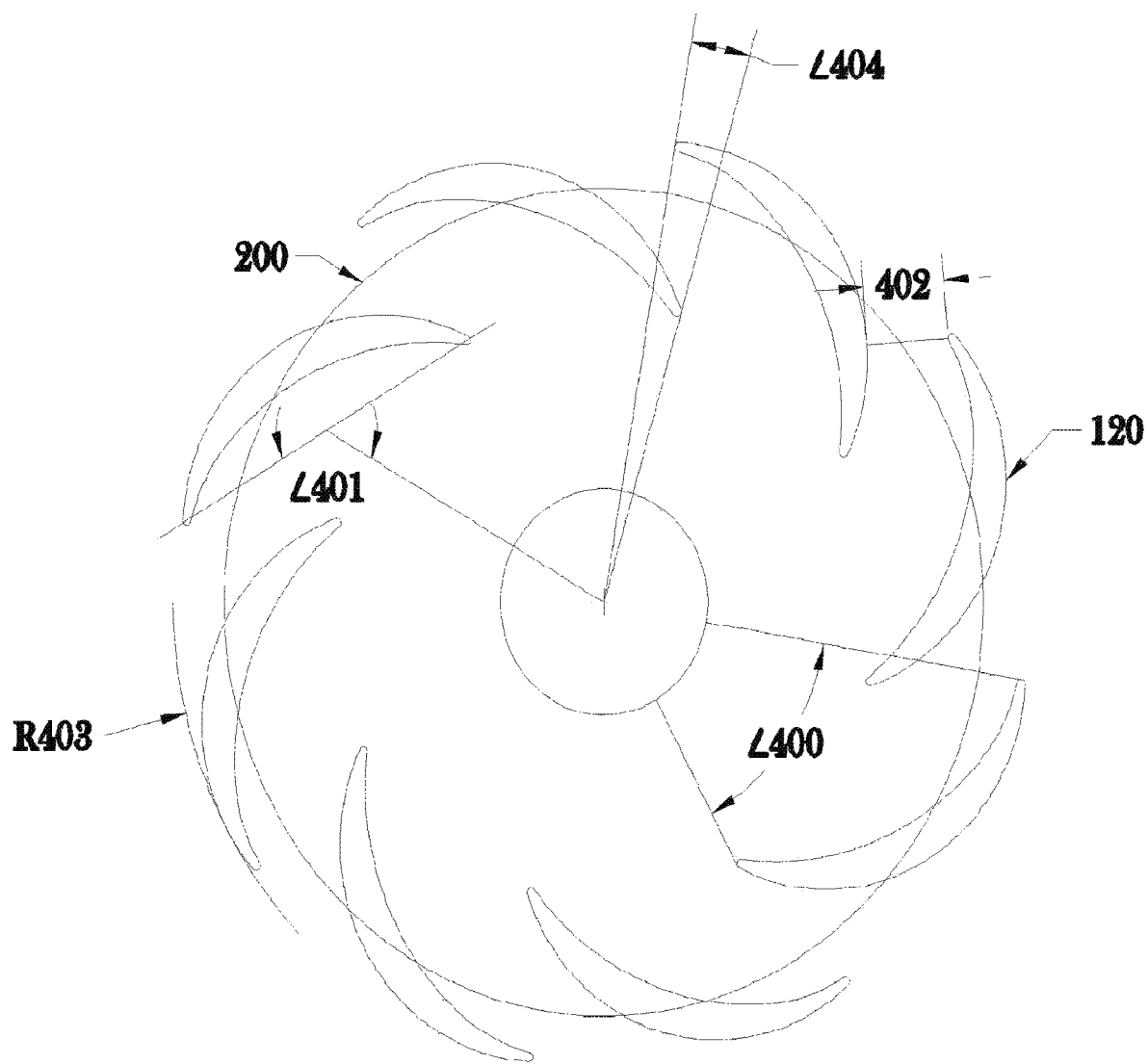
FIG. 13 is a cross sectional view one of one set of blades.

FIGS. 12 and 13 show an aspect of one of the preferred embodiments of the blade design wherein the concave portion of the shape 108 and the tilt of the blades <401 redirects and refocuses (reflects) at least some light that is not absorbed by upon the first contact with the PCO-reactive surface on to an outer surface of an adjacent blade, increasing the efficiency of the chamber. The blades 110 also overlap each other in the radial direction as can be seen by radius 200, drawing through the center point of each blade. This aspect reclaims some or all of the light that has previously been allowed to diffuse into the environment and provided a loss in the efficiency of the PCO reaction. This redirection and refocusing is calculated in two-dimensions by taking the radiation from the center of the lamp 120, measuring the angle against which the light comes in contact with the inner surface tangent 108 of the blade 110, and mirroring that angle of incidence across the tangent of the blade surface. This can also be derived from the outer surface of the lamp (since the light radiation takes place across the entirety of the lamp, not simply a geometric line running throughout the center of the lamp), but this simplified diagram shows the intent of this element of the preferred embodiment. Any embodiment in which light is redirected or refocused onto another surface coated with a PCO-reactive coating would be considered within the spirit of this invention. For this embodiment, a rotation angle of the blade 110 about the center of mass from (−3°) to (+9°) inclusive from the depicted embodiment would still direct the light impacting the inner surface of the blade 108 onto another PCO coated surface of the next blade (109) to accommodate manufacturing tolerances. Any two-dimensional section that geometrically redirects a vector emanating from a point in the light source against the tangent of a geometric figure comprising the reactor structure onto another desired point would be considered within the scope of this embodiment.

FIG. 13 shows the relationship of the blades 120 in cross section. Angle 400 shows the arc of emitted light that each blade is able to absorb. The pitch of each blade indicated by angle 401 can be adjusted to both redirect the refocused light onto a different portion of the blade in front of it, as well as adjust the flow of fluid through the reaction chamber. Distance between the blades indicated by line 402 allows for fluid to escape the reaction chamber at a controllable velocity and pressure. The radius of the largest point of the chamber indicated by line 403 controls the overall diameter of the reaction chamber. An overlap of the blades indicated by <404 is highly recommended, especially in chamber designs that include any sort of twist to the blades over the transverse length of the cell. Overlapping the blades allows for light to be refocused and redirected onto another PCO-reactive surface either on the reaction chamber or located outside of it if desired. Overlap of the blades will allow for tolerance in the manufacturing process; an overlap of 2-5° has been slightly beneficial, 6-8° has been optimal to reduce and/or prevent light escapage, but any overlap of 9+° has not shown much improvement over 8° of overlap. For this example of the current embodiment 7° of blade overlap has shown as optimal. ( The dimensions of the currently shown embodiments is:
<400—52.5°
<401—119.95°
402—0.2"
403—1.1"
<404—7°

FIG. 13 is a section cut of the very bottom of the tapered embodiment shown in FIG. 5.

Figure 14A:
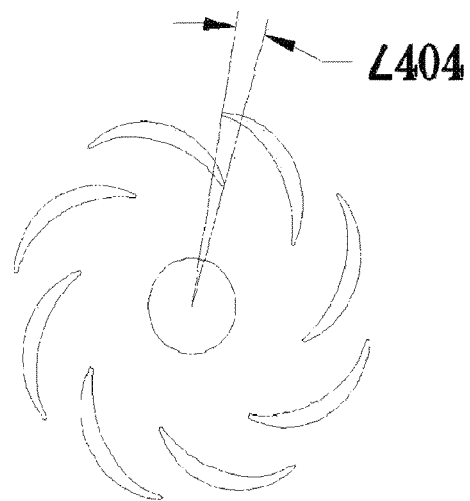
FIGS. 14a 14b and 14c are cross sectional views of three alternate designs of the blades.
Figure 14B:
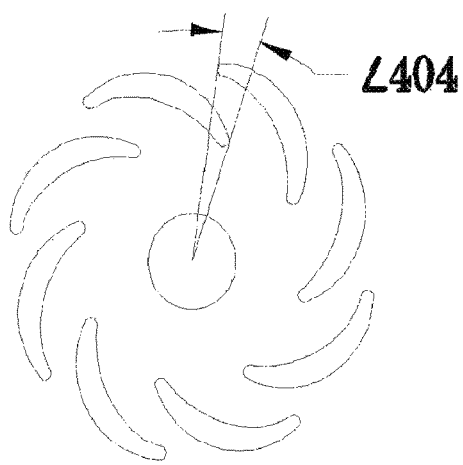
Figure 14C:
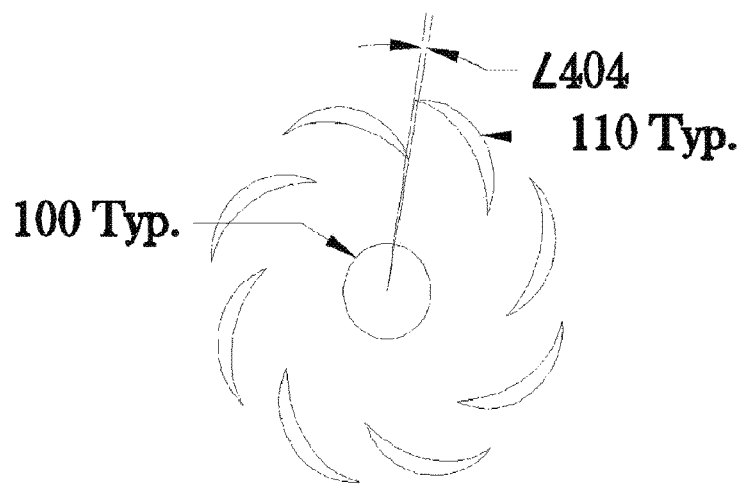

As can be seen in FIGS. 14*a-c*, various embodiments of the reaction chamber can have may require more or less overlap, at least partially dependent upon the twist of the blades and the desire to redirect a chosen amount of light, leading to the blade design with the highest efficiency for each circumstance. The disclosed embodiments have the ability to control the overlap based on the design of each blade as desired for any given situation. All of the disclosed elements of the disclosed housing, including blade shape, blade overlap, blade pitch, coating and chamber size can be varied to adapt to a given environment to create a chosen result. For example, to better accommodate the forces of a reaction chamber designed to be used with water (rather than air) being passed through, fewer, larger, thick blades may be desired, designing them such that the light is still refocused on another surface coated with PCO-reactive coating may be desired. Another example would be in a manufacturing process with loose tolerances, a greater overlap angle will reduce the amount of light escaping the reaction chamber without coming in contact with a PCO-reactive surface.

Figure 15:
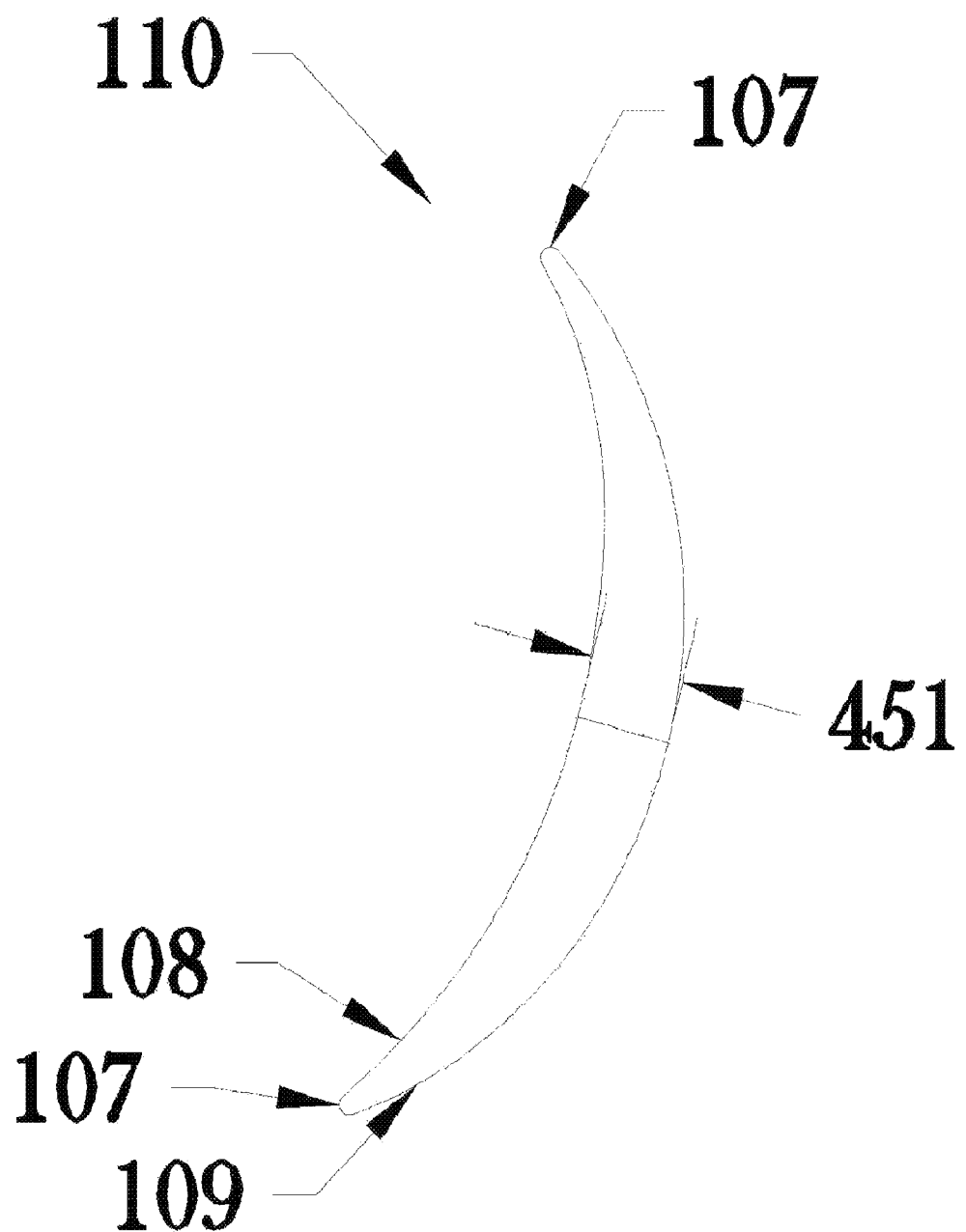
FIG. 15 is a close up of one of a cross section of one of the blades.

FIG. 15 is a detail view of blades 110 which can be formed with an interior (usually concave) surface 108 made up of straight line segments or concave arc, spline, or parabolic surfaces connected to an exterior (usually convex) surface 109 made up of straight line segments or concave arc, spline, or parabolic surfaces, connected by a straight or rounded connection 107. These surfaces 107, 108, 109 are not required to be symmetrical, and may be made up of a series of more complex shapes to achieve the desired characteristics for fluid flow, light control, and manufacturability. The difference between interior 108 and exterior 109 surfaces is the blade's thickness 451, which can vary over both the width and longitudinal extent of the blade. Varying this thickness will both change the structural characteristics of the chamber, but also will have an impact on the flow of the fluid across the surfaces of the blade. Utilizing similar characteristics to airfoils and hydrofoils (including Bernoulli's principle and Ventruri effect), the flow of the fluid across the inner surface 108 can be different than the flow across the outer surface 109. This can be a desired phenomenon to better control the fluid flow to improve the characteristics and efficiency of the PCO reaction.

Figure 16:
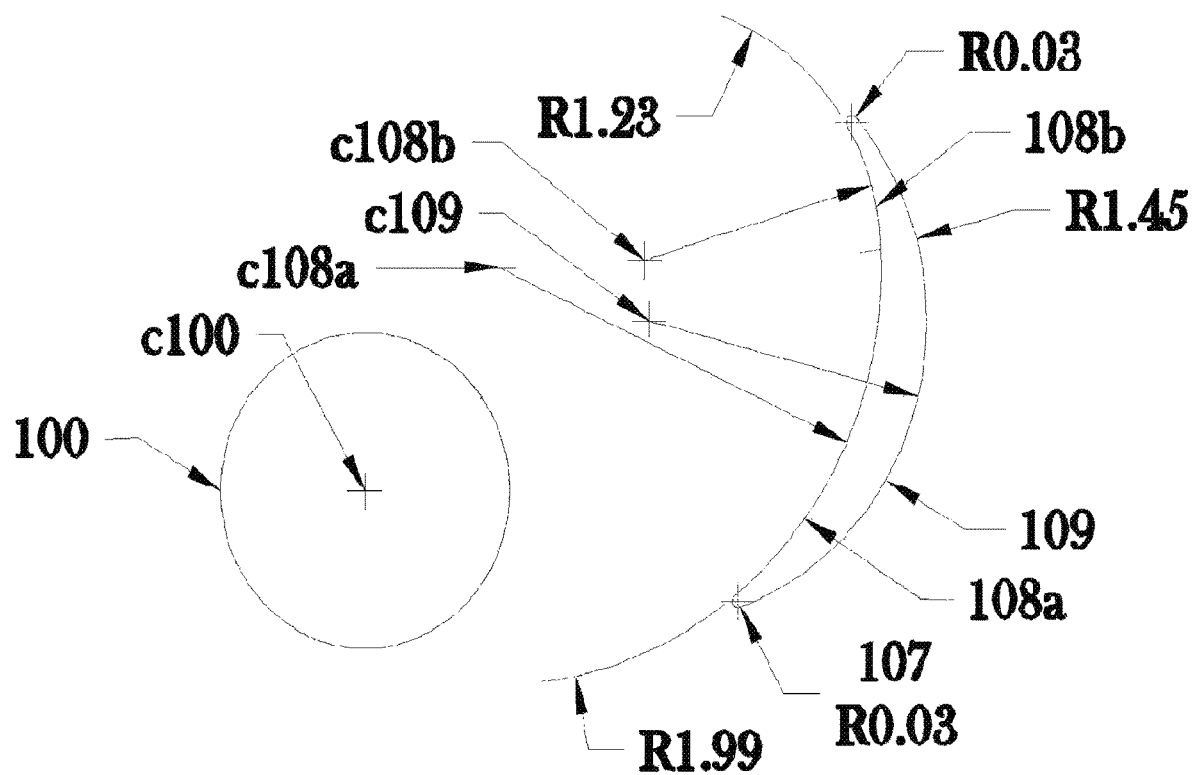
FIG. 16 is a close up cross sectional view a blade and the core.

FIG. 16 is a mathematical representation of the design of the embodiment of the blades shown in FIG. 5. These measurements are at the base of the blade design, and while are geometrically similar to section cuts throughout the cell, dimensions are given for the blades at their largest point (the base).

The inner surface 108 is comprised of two arcs 108a and 108b while the outer surface 109 is comprised of a single arc 109 in the depicted embodiment. Centers are given for each arc (c108a, c108b, c109), and coordinates are given for each of the surfaces from the center of the lamp (c100). Arc lengths are also given for each arc.

c108a–c100+1.27 @∠56.80° 80°
c108b–c100+1.82@∠37.06°
c109–c100+1.68@∠28.83°
108a=1.899
108b=0.6232
109=2.853

Any two-dimensional section that geometrically redirects and/or reflects a vector emanating from a point in the light source against the tangent of a geometric figure comprising the reactor structure onto another desired point would be considered within the scope of this embodiment. In the depicted embodiment, connecting surface 107 is a fillet with radius 0.03; center of this arc is not given, due its simplicity as a fillet, and small radius could lead to inaccuracy due to tolerance and rounding errors. Paired with information given in FIG. 13, a full representation of the two-dimensional blade design can be extrapolated. This blade design can be scaled to a different size, distorted or stretched, or modified from its base design. Any number of other measurements within the scope of the disclosure could be used as well, no limitation to the measurement is intended, or should be inferred.

Figure 17:
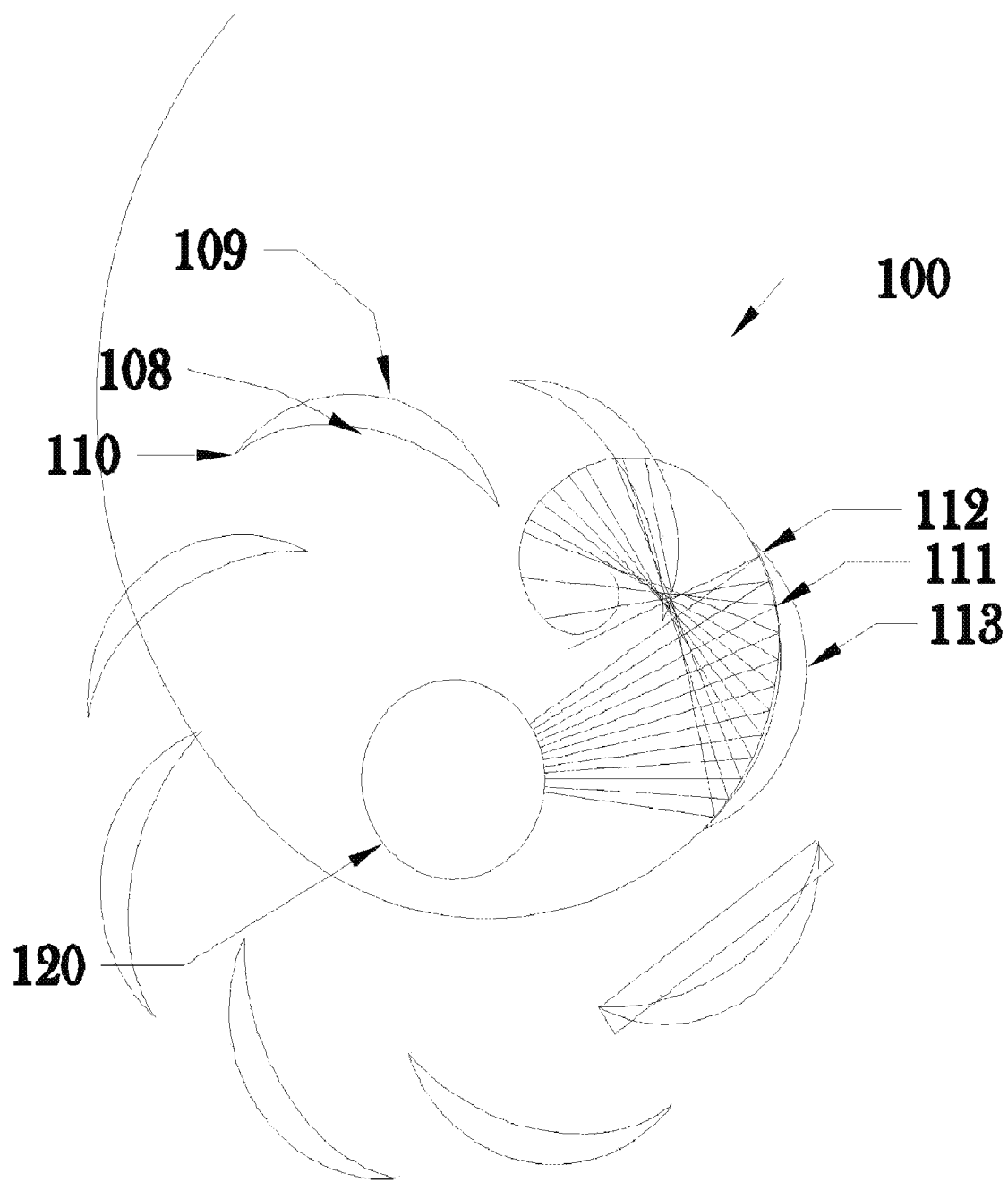
FIG. 17 shows the derivation of one possible inner surface of the blade via the Golden Section.

FIG. 17 is a representation of one derivation of the inner surface 108 redirection of light onto the outer surface 109 of the blade 110 next to it of it. It was done through an analysis of an approximation of what is commonly known as the Golden Section. While this is not a required characteristic of the embodiment of this object, this initial design was founded upon this approximation.

Figure 18:
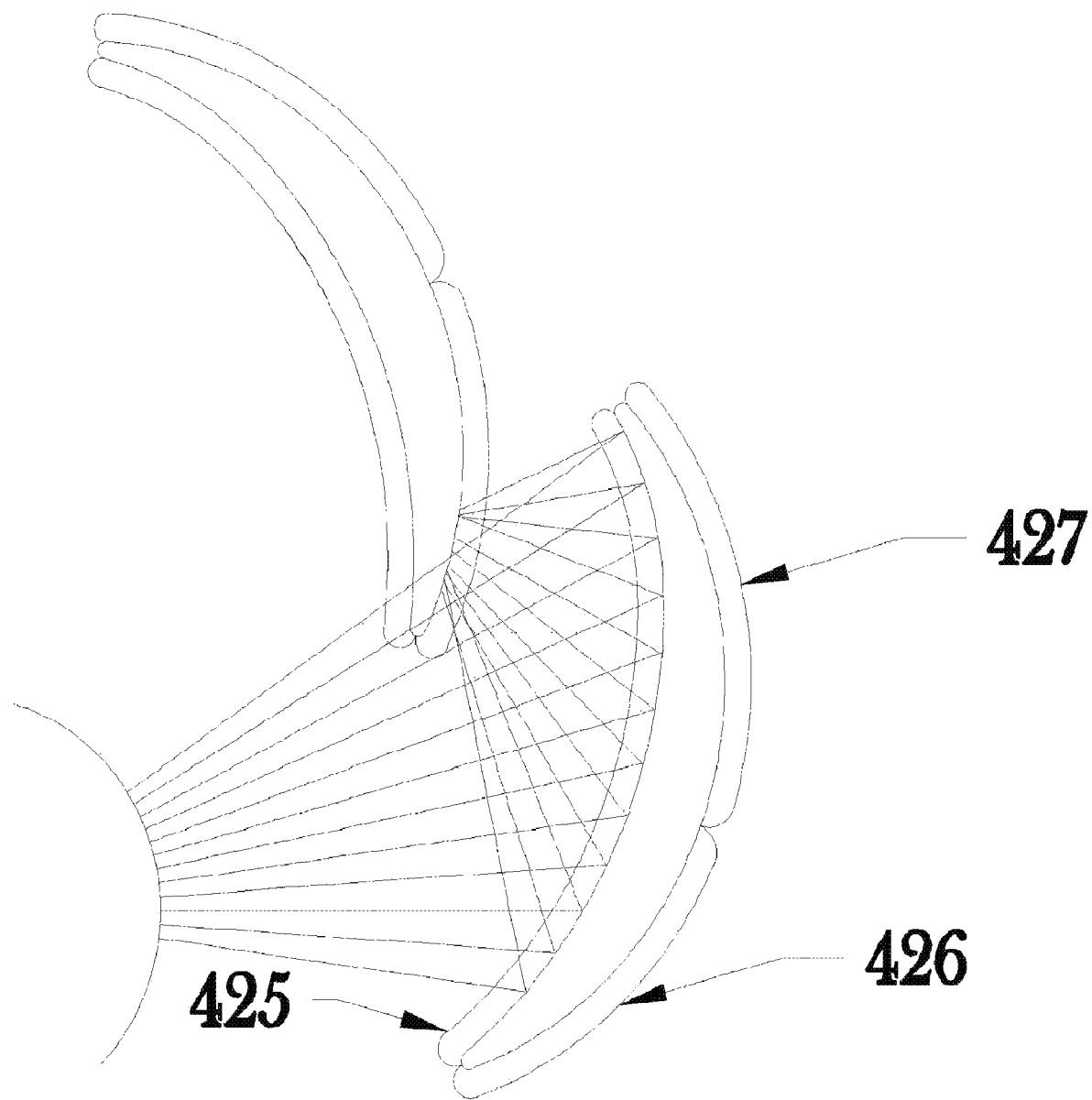
FIG. 18 is a detailed schematic view of a blade with multiple coatings.

FIG. 18 shows an additional embodiment variation of the disclosed designs. It is possible to coat different surfaces of any of the disclosed blades with different formulations of PCO-reactive coatings on different portions of each individual blade to achieve different reaction characteristics. One possible set of coating areas are depicted as a main reactive surface area (425), a secondary reactive surface area (426), and one or more tertiary reactive surface areas (427). The intent is that light will strike the main surface area (425) with full intensity, be either absorbed into the reaction as a photocatalyst or redirected onto the secondary surface area (426), which may have a different PCO-reactive coating specifically tailored to be more effective when irradiated by light with lower intensity than the coating across the main reactive surface area. The tertiary reactive surface areas may be coated with other formulations PCO-reactive coatings specifically designed to react with 'intermediary' substances (larger constituents not yet fully decomposed by the PCO reaction), break down specific molecules, or other reactive components which require little light to become photocatalytically active. Any number of possible variations of different surface coatings could be employed. No limitation to the depicted embodiment is intended or should be inferred.

Figure 19:
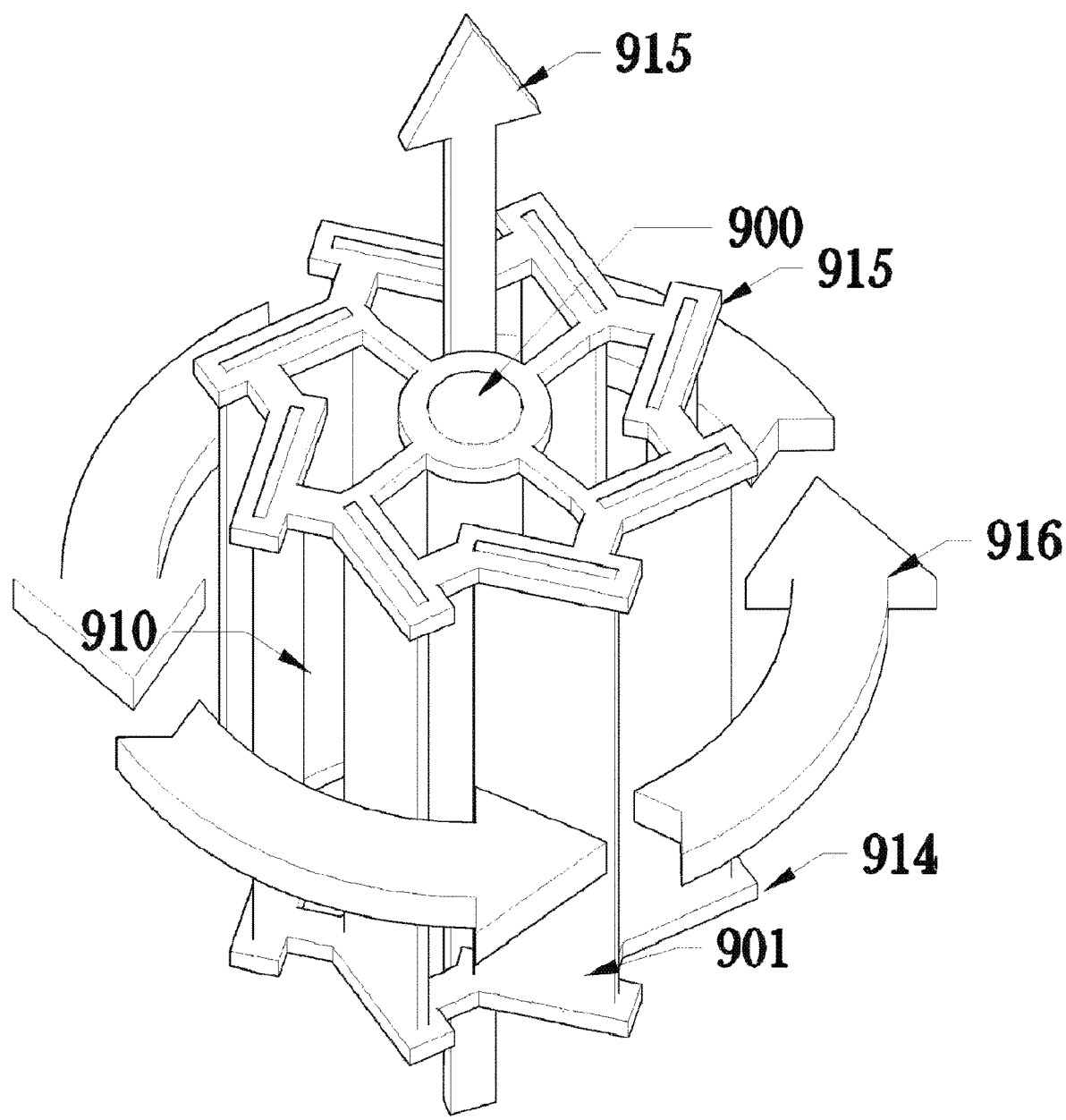
FIG. 19 is a perspective view of an alternate embodiment of one aspect of the invention where a housing is rotated to create air movement.

An alternate embodiment to the housing is depicted in FIG. 19. Air or other fluid is flowed through the housing 900 containing a light source 120 along the longitudinal axis, indicated by arrow 940, across the reactive surfaces 901 allowing the PCO reaction to take place. The housing 900 has a chosen number of blades 910 that extend along the longitudinal axis of the housing. The transverse profile of the blade 910 is flat These blades 910 are coated in a formulation of metal oxide or other coating as noted above. The blades 910 are held in place by a first retainer 915 and a second retainer 914 mounted on the ends of blades 910 as seen in FIG. 19. The light source 120 is mounted in the central axis of the housing as seen in FIG. 2. The light source 120 depicted is a T-5 UV light bulb. A wide range of acceptable light sources are known in the art, no limitation to the depicted embodiment is intended or should be inferred. With this embodiment the housing 900 is rotated in the direction of arrow 916 to create airflow through the housing shown by arrow 914. The flat profile of the blades in the depicted embodiment will reduce the amount of refection of the unused UV light, but the tilt of the blades will still allow come of that occur. The overlap of the blades in the radial direction is also not requirement in this embodiment.

While a number of exemplary aspects and embodiments have been discussed above, those of skill in the art will recognize certain modifications, permutations, additions and sub-combinations therefore. It is therefore intended that the following appended claims hereinafter introduced are interpreted to include all such modifications, permutations, additions and sub-combinations are within their true spirit and scope. Each apparatus embodiment described herein has numerous equivalents.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Whenever a range is given in the specification, all intermediate ranges and subranges, as well as all individual values included in the ranges given are intended to be included in the disclosure.

In general the terms and phrases used herein have their art-recognized meaning, which can be found by reference to standard texts, journal references and contexts known to those skilled in the art. The above definitions are provided to clarify their specific use in the context of the invention.

I claim:

1. A photocatalytic reactor housing comprising:
a frame holding a light source, the light source extending along a longitudinal axis of the photocatalytic reactor housing;
a plurality of blades substantially encompassing the light source around the longitudinal axis, the plurality of blades spaced apart from the light source allowing a fluid to flow through a space formed therebetween, and the plurality of blades fixed such that the plurality of blades cannot rotate with respect to the light source;
each blade having an interior surface facing the light source, an exterior surface opposite the interior surface facing away from the light source, a length extending along the longitudinal axis, and a width extending around the light source in a transverse plane perpendicular to the longitudinal axis;
at least a portion of the surfaces of the plurality of blades having a coating of material with photocatalytic oxidative properties; and
the interior surface of each blade is configured to redirect and refocus some amount of light emitted by the light source onto the exterior surface of an adjacent blade;
wherein a fluid flow is conveyed through the photocatalytic reactor housing along the longitudinal axis.

2. The photocatalytic reactor housing of claim 1, wherein each blade is tilted along at least a portion of the width with respect to a radial direction extending outward from the longitudinal axis in the traverse plane.

3. The photocatalytic reactor housing of claim 1, wherein the interior surface of at least some of the plurality of blades has a concave shape comprised of a first arc and a second arc.

4. The photocatalytic reactor housing of claim 3, wherein the plurality of blades twist along the longitudinal axis.

5. The photocatalytic reactor housing of claim 3, wherein each blade has an arch shaped cross section for at least a portion of the length along the longitudinal axis.

6. The photocatalytic reactor housing of claim 1, wherein the width of each blade tapers along at least a portion of the length along the longitudinal axis.

7. The photocatalytic reactor housing of claim 1, wherein an outer radius of the photocatalytic reactor housing reduces along at least a portion of the longitudinal axis which houses the plurality of blades.

8. The photocatalytic reactor housing of claim 1, wherein at least some of the plurality of blades overlap in a radial direction of the longitudinal axis.

9. The photocatalytic reactor housing of claim 1, further comprising at least a portion of the surface of at least one blade having a coating of a second material with photocatalytic oxidative properties, the first and second materials having different photocatalytic properties.

10. The photocatalytic reactor housing of claim 9, wherein the first material is located on the interior surfaces of the plurality of blades and the second material is located on the exterior surfaces of the plurality of blades.

11. The photocatalytic reactor housing of claim 9, wherein the first material is located every other blade and the second material is located on the remaining blades.

12. The photocatalytic reactor housing of claim 9, further comprising at least a portion of the surface of at least one blade having a coating of third material with photocatalytic oxidative properties, the first, second and third materials having different photocatalytic properties.

13. The photocatalytic reactor housing of claim 1, wherein the width of each blade at least partially overlaps the width of an adjacent blade in a radial direction, the radial direction extending in the traverse plane from an origin point located at the longitudinal axis outward in a straight line.

14. The photocatalytic reactor housing of claim 1, wherein the interior surfaces of the plurality of blades have transverse profiles shaped as straight line segments, arcs, splines, or parabolic surfaces.

15. The photocatalytic reactor housing of claim 1, wherein the exterior surfaces of the plurality of blades have transverse profiles shaped as straight line segments, arcs, splines, or parabolic surfaces.

16. The photocatalytic reactor housing of claim 1, wherein the interior surface is positioned relative to the light source to provide an angle of incidence such that a ray of light reflected by the interior surface in the transverse plane is reflected directly onto the exterior surface of the adjacent blade, the ray of light being emitted from the light source coincident with a geometric line extending through a center of the light source.

17. The photocatalytic reactor housing of claim 1, wherein the plurality of blades are at least coextensive in length with a light-emitting surface of the light source along the longitudinal axis.

* * * * *